US007993836B2

(12) United States Patent
Papassotiropoulos et al.

(10) Patent No.: US 7,993,836 B2
(45) Date of Patent: Aug. 9, 2011

(54) GENES AFFECTING HUMAN MEMORY PERFORMANCE

(75) Inventors: Andreas Papassotiropoulos, Zurich (CH); Dietrich Stephan, Phoenix, AZ (US); Dominique J.-F. De Quervain, Zurich (CH)

(73) Assignees: Translational Genomics Research Institute, Phoenix, AZ (US); University of Zurich, Zurich (CH)

( * ) Notice: Subject to any disclaimer, the term of this patent is extended or adjusted under 35 U.S.C. 154(b) by 67 days.

(21) Appl. No.: 12/162,262

(22) PCT Filed: Jan. 26, 2007

(86) PCT No.: PCT/US2007/061112
§ 371 (c)(1),
(2), (4) Date: Mar. 5, 2009

(87) PCT Pub. No.: WO2007/120955
PCT Pub. Date: Oct. 25, 2007

(65) Prior Publication Data
US 2009/0227500 A1 Sep. 10, 2009

Related U.S. Application Data

(60) Provisional application No. 60/762,713, filed on Jan. 27, 2006, provisional application No. 60/862,194, filed on Oct. 19, 2006.

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search .................. None
See application file for complete search history.

(56) References Cited

U.S. PATENT DOCUMENTS

| | | | |
|---|---|---|---|
| 4,634,770 | A | 1/1987 | Hidaka et al. |
| 4,678,783 | A | 7/1987 | Hidaka et al. |
| 4,709,032 | A | 11/1987 | Hidaka et al. |
| 4,798,897 | A | 1/1989 | Hidaka et al. |
| 5,942,505 | A | 8/1999 | Kawakubo et al. |
| 6,699,508 | B1 | 3/2004 | Sugi et al. |
| 7,125,567 | B2 | 10/2006 | Sugi et al. |
| 2006/0280793 | A1 | 12/2006 | Sugi et al. |
| 2008/0108568 | A1 | 5/2008 | Stephan et al. |

FOREIGN PATENT DOCUMENTS

| | | |
|---|---|---|
| EP | 0 187 371 | 6/1991 |
| JP | 6-293643 A | 10/1994 |
| WO | WO 02/22819 | 3/2002 |
| WO | WO 2005/017896 A1 | 2/2005 |

OTHER PUBLICATIONS

Juppner H. Bone (Aug. 1995) vol. 17, No. 2, Supplement, pp. 39S-42S.*
Hacker U.T. et al. Gut (May 1997) vol. 40, No. 5, pp. 623-627.*
Pennisi E. Science (Sep. 18, 1998) vol. 281, pp. 1787-1789.*
Need A.C. et al. American Journal of Medical Genetics Part B (Neuropsychiatric Genetics) 147B:667-668 (2008).*
European Search Report issued in application No. EP 07 77 7651 on Jan. 4, 2010.
Database Geneseq [Online] "Cyclin-dependent kinase modulation biomarker SEQ ID No. 787," XP002560639, retrieved from EBI accession No. GSP:ADX06222, Apr. 21, 2005.
Database UniProt [Online] "RecName: Full=ProteinWWC1; AltName: Full = WW domain-containing protein 1; AltName: Full=Kidney and brain protein; Short=KIBRA; AltName: Full-HBeAg-binding protein 3," XP002560640, retrieved from EBI accession No. UNIPROT:Q8IX03, Mar. 1, 2003.
Levin et al., "Memory Decline of Aging Reduced by Extracellular Superoxide Dismutase Overexpression," *Behavior Genetics*, vol. 35, No. 4, pp. 447-453, Jul. 2005.
Schneider et al., "KIBRA: a new gateway to learning and memory?", Frontiers in aging Neuroscience, Review Article, Feb. 2010, vol. 2, Article 4, pp. 1-9.
McClearn et al., Substantial Genetic Influence on Cognitive Abilities in Twins 80 or More Years Old, Science vol. 276, pp. 1560-1563, 1997.
de Quervain et al., A Functional Genetic Variation of the 5-HT2a Receptor Affects of Human Memory, Nature Neuroscience, vol. 6, No. 11, pp. 1141-1142, 2003.
A. Papassotiropoulos et al., The Prion Gene is Associated with Human Long-Term, Memory, Human Molecular Genetics, vol. 14, No. 15, pp. 2241-2246, 2005.
Schork, Genome Partitioning and Whole-Genome Analysis, Advances in Genetics, vol. 42, pp. 299-322, 2001.
Kelsoe, Genomics and the Human Genome Project: Implications for Psychiatry, International Review of Psychiatry, 16(4), pp. 294-300, 2004.
Watson et al. Molecular Biology of the Gene, 4th Edition, 1987, Benjamin/Cummings, p. 224-227.
Kremerskothen et al., Characterization of KIBRA, a Novel WW Domain-Containing Protein, Biochemical and Biophysical Research Communications 300, pp. 862-867, 2003.
Dudai, Molecular Bases of Long-Term Memories: A Question of Persistence, Current Opinion in Neurobiology 12 pp. 211-216, 2002.
Büther et al., KIBRA is a Novel Substrate for Protein Kinase C$\zeta$, Biochemical and Biophysical Research Communications 317, pp. 703-707, 2004.
J. Rizo et al., $C_2$-domains, Structure and Function of a Universal $Ca^{2+}$-binding Domain, The Journal of Biological Chemistry, vol. 273, No. 26, pp. 15879-15882, 1998.
J. Ubach et al., $Ca^{2+}$ Binding to Synaptotagmin: How Many $Ca^{2+}$ ions Bind to the Tip of a $C_2$-domain?, The EMBO Journal vol. 17 No. 14 pp. 3921-3930, 1998.
G. Hintsch et al., The Calsyntenins—A Family of Postsynaptic Membrane Proteins with Distinct Neuronal Expression Patterns, Molecular and Cellular Neuroscience 21, pp. 393-409, 2002.

(Continued)

*Primary Examiner* — Stephen Kapushoc
(74) *Attorney, Agent, or Firm* — Foley & Lardner LLP

(57) ABSTRACT

The present invention relates to DNA sequences associated with human memory performance. It also provides methods for (i) screening for diseases and pathological conditions affecting human memory, (ii) identifying agents useful for treatment of diseases and pathological conditions affecting human memory, and (iii) agents and compositions useful for treatment of diseases and pathological conditions affecting human memory.

8 Claims, 5 Drawing Sheets

OTHER PUBLICATIONS

Need et al., Failure to Replicate Effect on Kibra on Human Memory in Two Large Cohorts of European Origin, Am J Med Genet Part B, 2007.

Nagase et al., Prediction of the Coding Sequences of Unidentified Human Genes. XII. The Complete Sequences of 100 New cDNA Clones from Brain Which Code for Large Proteins in vitro, DNA Research 5, pp. 355-364, 1998.

Nacmias et al., KIBRA Gene Variants are Associated with Episodic Memory Performance in Subjective Memory Complaints, Neuroscience Letters 436 pp. 145-147, 2008.

Almeida et al., KIBRA Genetic Polymorphism Influences Episodic Memory in Later Life, but Does Not Increase the Risk of Mild Cognitive Impairment, 2007.

Schaper et al., KIBRA Gene Variants are Associated with Episodic Memory in Healthy Elderly, Neurobiology of Aging 29, pp. 1123-1125, 2008.

Rodriguez-Rodriguez et al., Age-Dependent Association of KIBRA Genetic Variation and Alzheimer's Disease Risk, Neurobiological of Aging, 2007.

Papassotiropoulos et al., Common KIBRA Alleles are Associated with Human Memory Performance, Science, vol. 314, pp. 475-478, 2006.

Galkin et al., "CVS-3983, a selective matriptase inhibitor, suppresses the growth of androgen independent prostate tumor xenografts." Prostate, 2004, 61(3):228-235.

Kamei et al., "Evaluation of Fasudil Hydrochloride Treatment for Wandering Symptoms in Cerebrovascular Dementia with 31P-Magnetic Resonance Spectroscopy and Xe-Computed Tomography." Clinical Neuropharmacology, vol. 19, No. 5: 428-438, 1996.

Kanoh et al., "Thiazolidinedione treatment enhances insulin effects on protein kinase C-zeta/lambda activation and glucose transport in adipocytes of nondiabetic and goto-kakizaki type II diabetic rats." J. Biol. Chem., 2000, 275(22):16690-16696.

Papassotiropoulos et al., "Common *kibra* alleles are associated with human memory performance." Science, Oct. 20, 2006, vol. 314:475-478.

Qatsha et al., "Go 6976, a selective inhibitor of protein kinase C, is a potent antagonis human immunodeficiency virus 1 induction from latent/low-level-prod reservoir cells in vitro." Proc. Nat'l. Acad. Sci., May 15, 2003, 90(10):4674-4678.

Rena, "D4476, a cell-permeant inhibitor of CK1, suppresses the site-specific phosphorylation and nuclear exclusion of FOXO1a." EMBO, 2004, vol. 5(1):60-65.

Sajan, M. "Protein kinase C-ζ and phosphoinositide-dependent kinase-1 are required for the insulin-induced activation of ERK in rat adipocytes." J. Biol. Chem, 1999, 274(43):30495-30500.

Schmitz-Peiffer, C., et al., "Activated protein kinase C alpha associates with annexin VI from skeletal muscle." Biochem. Journal, 1998, vol. 330: 675-681.

Standaert et al., "Okadaic acid activated atypical protein kinase C (ζ λ) in rat and 3T3/L 1 adipocytes." J. Biol. Chem., 1999, 274(20):14074-14078.

Tsien, Joe, "The Memory Code (extended version)". Scientific American, Jun. 17, 2007.

von Willebrand et al., "The Tyrphostin AG1024 accelerates the degradation of phosphorylated forms of retinoblastoma protein (pRb) and restores pRb tumor suppressive function in melanoma cells." Cancer Research 63, 1420-1429, Mar. 15, 2003.

Zhou et al., "Nucleolin is a protein kinase C-zeta substrate. Connection between cell surface signaling and nucleus in PC12 cells." J. Biol. Chem, 1997, 272(49):31130-31137.

Goodman, Ann B., Retinoid Receptors, Transporters, and Metabolizers as Therapeutic Targets in Late Onset Alzheimer Disease, J. Cellular Physiology, vol. 209, No. 3: pp. 298-306, 2006.

Dash et al., "A role for hippocampal Rho-ROCK pathway in long-term spatial memory", Biochemical and Biophysical Research Communications 322, 2004, 893-898.

Lamprecht et al., "Fear Memory Formulation Involves p190 RhoGAP and ROCK Proteins through a GRB2-Mediated Complex", Neuron, vol. 36, 2002, 727-738.

Schulz et al. "The CLN9 Protein, a Regulatory of Dihydroceramide Synthase", Journal of Biological Chemistry, 2006, vol. 281, No. 5, pp. 2784-2794.

International Search Report from PCT/US07/75728, mailed Sep. 5, 2008.

O'Kane et al., "Increased long-term potentiation in the CA1 region of rat hippocampus via modulation of GTPase signaling or inhibition of Rho kinase," *Neuropharmacology*, vol. 46, pp. 879-887 (2004).

Niisato et al., "Age-Dependent Enhancement of Hippocampal Long-Term Potentiation and Impairment of Spatial Learning through the Rho-Associate Kinase Pathway in Protein Tyrosine Phosphatase Receptor Type Z-Deficient Mice," *The Journal of Neuroscience*, vol. 25, No. 5, pp. 1081-1088 (Feb. 2, 2005).

Tamura et al., "Protein tyrosine phospatase receptor type Z is involved in hippocampus-dependent memory formation through dephosphorylation at Y1105 on p190 RhoGAP," *Neuroscience Letters*, vol. 399, pp. 33-38 (2006).

Office Action issued on Nov. 30, 2009, by the Examiner in U.S. Appl. No. 11/837,326.

* cited by examiner

Figure 1

Influence of SNPs rs17070145 (*KIBRA*) and rs6439886 (*CLSTN2*) on verbal episodic memory in the Swiss population

|  | Immediately recalled words (mean ± s.e) | Words recalled after 5 min (mean ± s.e) | Words recalled after 24 h (mean ± s.e) |
| --- | --- | --- | --- |
| rs17070145* | | | |
| C/C, n = 164 | 23.6 ± 0.3 | 7.6 ± 0.2$^a$ | 6.7 ± 0.2$^b$ |
| C/T & T/T, n = 169 | 24.1 ± 0.3 | 9.4 ± 0.2$^a$ | 8.0 ± 0.2$^b$ |
| | | | |
| rs6439886 | | | |
| T/T, n = 265 | 23.9 ± 0.2 | 8.4 ± 0.2$^c$ | 7.3 ± 0.2$^d$ |
| T/C & C/C, n = 76 | 24.2 ± 0.4 | 9.8 ± 0.4$^c$ | 8.4 ± 0.4$^d$ |

Means with common superscripts are significantly different.

* Genotype calls of 8 subjects failed to pass the quality control criteria.

Influence of SNPs rs17070145 (*KIBRA*) and rs6439886 (*CLSTN2*)
on verbal episodic memory in the US population*

|  | Immediately recalled words (AVLT) (mean ± s.e) | Words recalled after 30 min (AVLT) (mean ± s.e) | Free recall of words (SRT) (mean ± s.e) |
|---|---|---|---|
| rs17070145 | | | |
| C/C, $n$ = 126 | 9.4 ± 0.3 | 8.5 ± 0.3[a] | 83.7 ± 1.2[b] |
| C/T & T/T, $n$ = 130 | 10.0 ± 0.3 | 9.7 ± 0.3[a] | 90.3 ± 1.1[b] |
| rs6439886[#] | | | |
| T/T, $n$ = 185 | 9.7 ± 0.2 | 9.1 ± 0.2 | 88.4 ± 0.9 |
| T/C & C/C, $n$ = 64 | 9.9 ± 0.4 | 9.2 ± 0.4 | 88.9 ± 1.6 |

Means with common superscripts are significantly different.

* The SRT was completed by 200 participants (98 C/C carriers and 102 C/T & T/T carriers of rs17070145))

[#]: Genotype calls of 7 subjects failed to pass the quality control criteria.

[a]: $P$ = 0.004, [b]: $P$ = 0.00005

Significance of SNPs and haplotypes

KIBRA allele-dependent differences in hippocampal activation

GENES AFFECTING HUMAN MEMORY PERFORMANCE

CROSS-REFERENCE TO RELATED PATENT APPLICATIONS

This application is a National Phase Entry of PCT/US2007/061112 filed Jan. 26, 2007, which claims priority to U.S. Provisional Application No. 60/862,194 filed Oct. 19, 2006 and U.S. Provisional Application No. 60/762,713 filed Jan. 27, 2006, all incorporated herein by reference in their entireties.

FIELD OF THE INVENTION

This invention relates to DNA sequences associated with human memory performance. This invention further relates to (i) methods for screening for diseases and pathological conditions affecting human memory, (ii) methods for identifying agents useful for treatment of diseases and pathological conditions affecting human memory, and (iii) agents and compositions useful for treatment of diseases and pathological conditions affecting human memory.

BACKGROUND OF THE INVENTION

Human memory is a polygenic cognitive trait. Heritability estimates of approximately fifty percent (50%) suggest that naturally occurring genetic variability has an important impact on this fundamental brain function. (G. E. McClearn et al., Science 276, 1560 (1997)). Recent candidate-gene association studies have successfully identified some genetic variations with significant impact on human memory capacity and human memory performance. (D. J. de Quervain et al., Nat. Neurosci. 6, 1141 (2003); A. Papassotiropoulos et al. Hum. Mol. Genet. 14, 2241 (2005)). However, the success of such hypothesis-driven studies strongly depends upon pre-existing information, which limits their potential to identify novel genes and molecular pathways. (N. J. Schork, Adv. Genet. 42, 299 (2001); J. R. Kelsoe, Int. Rev. Psychiatry 16, 294 (2004)). To date, an unbiased hypothesis-free search of the whole genome for human memory-controlling genes has not been performed. Therefore, there is a clear unmet need in the art to identify genes and genetic variations associated with human memory.

SUMMARY OF THE INVENTION

The present invention arises from whole-genome genetic association studies performed in two particular human populations to detect specific single nucleotide polymorphisms within genomic regions implicated in human memory function.

In one aspect of the present invention, genomic regions encoding the neuronal protein KIBRA and genomic regions encoding the synaptic protein Calsyntenin 2 (CLSTN2), as well as various single nucleotide polymorphisms within the KIBRA and CLSTN2 genes taught by the present invention, are used to modulate human memory function.

In another aspect, methods for screening for diseases and pathological conditions affecting human memory are provided.

In an additional aspect, methods for identifying agents useful for treatment of diseases and pathological conditions affecting human memory are provided. Such agents are identified based on their ability to modulate human memory function.

Finally, in yet another aspect of the present invention, agents and compositions useful for treatment of diseases and pathological conditions affecting human memory are provided. Such agents are also useful as lead compounds for designing or searching for additional drugs and pharmaceutical compositions to treat diseases and pathological conditions related to human memory function.

BRIEF DESCRIPTION OF THE DRAWINGS

The following invention will become better understood with reference to the specification, appended claims, and accompanying drawings, where:

FIG. 1. Table describing the influence of single nucleotide polymorphisms (SNPs) rs17070145 (KIBRA) and rs6439886 (CLSTN2) on verbal episodic memory in the Swiss population.

FIG. 2. Table describing the influence of SNPs rs17070145 (KIBRA) and rs6439886 (CLSTN2) on verbal episodic memory in the U.S. population.

DETAILED DESCRIPTION OF THE INVENTION

Definitions

Figure 3:
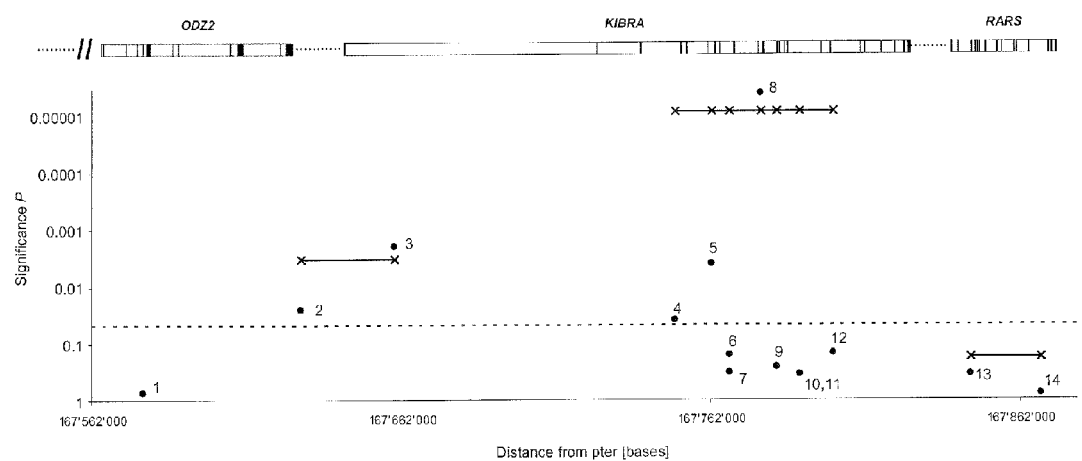
FIG. 3. Significance of SNPs and haplotypes. Fourteen common SNPs were used to fine-map the region harboring KIBRA, RARS, and part of ODZ2. High levels of linkage disequilibrium (P<0.001) were detected between SNPs 2 and 3, between SNPs 4 and 12, and between SNPs 13 and 14. SNP 8 and the corresponding haplotype yielded the highest significance levels (P=0.000004 and P=0.000008, respectively). Dots represent SNPs, continuous horizontal lines represent haplotypes, and the dotted line represents the 0.05 significance level.
1: rs1363560, 2: rs7727920, 3: rs2279698, 4: rs11738934, 5: rs6862868, 6: rs2241368, 7: rs17551608, 8: rs170701459: rs4976606, 10: rs3822660, 11: rs3822659, 12: rs3733980, 13: rs244903, 14: rs10516047
Figure 4:
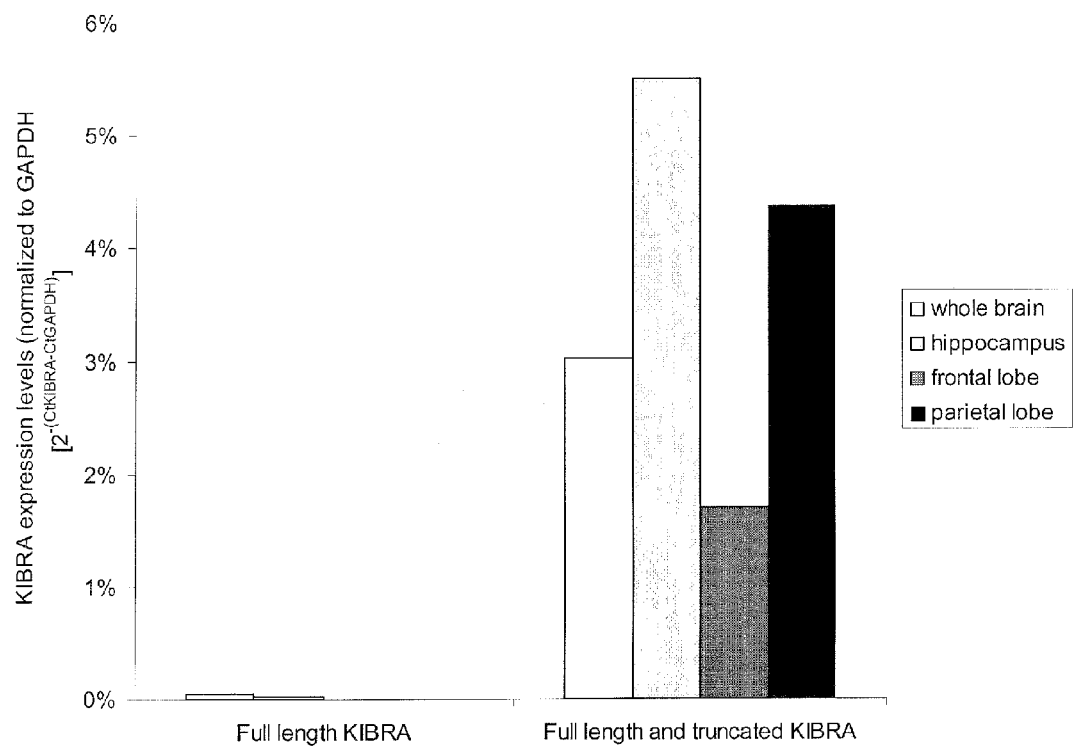
FIG. 4. KIBRA expression levels in human whole brain homogenate, hippocampus, frontal and parietal lobe evaluated by qRT-PCR and normalized to GAPDH expression levels. Expression levels of full-length KIBRA in the human brain were low (figure left). In contrast, expression levels of truncated KIBRA were high in all brain regions examined, with highest levels in the hippocampus (figure right). Three primer combinations were used for the quantification of expression levels. The first combination recognized only full length KIBRA transcripts; the second detected both full length KIBRA and its truncated version (KIAA0869). A third primer combination was used to rule out genomic contamination.
Figure 5:
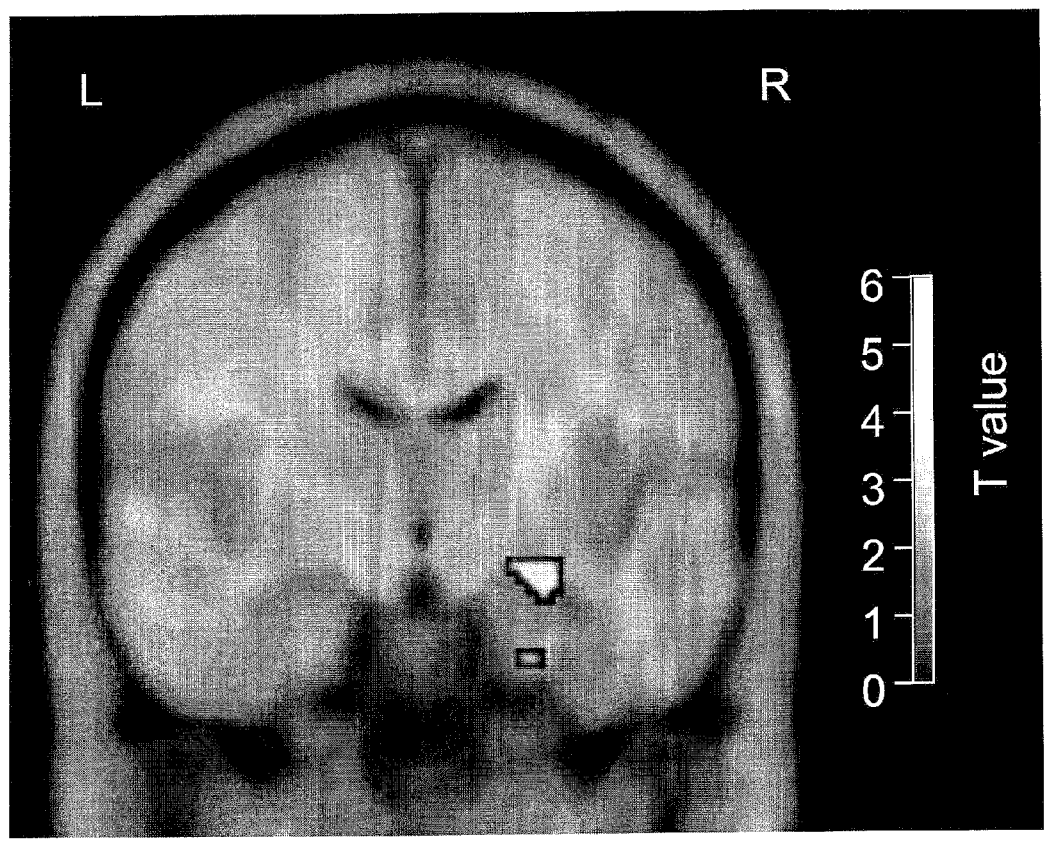
FIG. 5. KIBRA allele-dependent differences in hippocampal activation. fMRI was performed in 30 healthy human subjects (15 T allele carriers, 15 non-carriers of the T allele of SNP rs17070145) during episodic memory retrieval. The genotype groups were matched for age, sex, education. Groups were also matched for recall performance to study genotype-dependent differences in memory-related brain activity independently of differential performance. In comparison with non-carriers of the T allele, T allele carriers had significantly greater memory-related increases in hippocampal brain activity. Threshold: P<0.001. Large activation: hippocampus, small activation: parahippocampus.

In accordance with the present invention and as used herein, the following terms and abbreviations are defined with the following meanings, unless explicitly stated otherwise.

These explanations are intended to be exemplary only. They are not intended to limit the terms as they are described or referred to throughout the specification. Rather, these explanations are meant to include any additional aspects and/or examples of the terms as described and claimed herein.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA). As used herein, the terms "encoding" or "encoded" when referring to a protein or polypeptide of defined sequence include all nucleic acid sequences that encode the protein or polypeptide of defined sequence, including nucleic acid sequences that differ from the naturally-occurring sequence by the degeneracy of the genetic code, unless such sequences are excluded. It is well known in the art that many amino acids are encoded by multiple codons, and that many nucleic acid sequences can therefore encode the same protein or polypeptide sequence.

As used herein, "full-length sequence" in reference to a specified polynucleotide or its encoded protein means having the entire nucleic acid sequence or the entire amino acid sequence of a native sequence. By "native sequence" is intended an endogenous sequence, i.e., a non-engineered sequence found in an organism's genome. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids. In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see. e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gin or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or lie), leucine (L or Leu), methionine (M or Mct), valine (V or Val); and (6) phenylalanine (F or Phe), tyrosine (Y or Tyr), tryptophan (W or Trp); (see also, e.g., Creighton (1984) Proteins, W.H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

As used herein to refer to a protein or nucleic acid molecule, the terms "isolated" and/or "purified" are used interchangeably to refer to a state in which the protein or nucleic acid molecule of interest is typically found in nature, and in which the protein or nucleic acid molecule of interest is substantially free of other molecules that would interfere with the activity of the protein or nucleic acid molecule that is being assayed or employed.

For example, the term "purified" can refer to a preparation in which the protein or nucleic acid molecule of interest is 50%. 60%, 70%, 75%, 80%, 85%, 90%, 95%, 97.5%, 99%, 99.9%, or 99.99% pure, or one of still greater purity. Methods for the isolation of protein and nucleic acid molecules are well known in the art.

As used herein the term "recombinantly engineered" or "engineered" connotes the utilization of recombinant DNA technology to introduce (e.g., engineer) a change in the protein structure based on an understanding of the protein's mechanism of action and a consideration of the amino acids being introduced, deleted, or substituted.

As used herein, the terms "single nucleotide polymorphism" or "SNP" are used interchangeably to refer to a DNA sequence variation that occurs when a single nucleotide (A, T, C, or G) in the genome is altered. SNPs can occur in both coding (gene) and noncoding regions of the genome.

As used herein, the term "haplotype" refers to a set of genes at more than one locus or a genomic region containing linked polymorphisms which is inherited by an individual from one of its parents.

As used herein, the term "linkage disequilibrium" refers to a condition where the observed frequencies of haplotypes in a population do not agree with haplotype frequencies predicted by multiplying together the frequency of individual genetic markers in each haplotype.

As used herein, the term "comprising" means including, but not limited to, whatever follows the word "comprising". Thus, use of the term "comprising" indicates that the listed elements are required or mandatory, but that other elements are optional and may or may not be present.

As used herein, the term "consisting of" means including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

One embodiment of the present invention is a method for assessing memory performance in a patient comprising the steps of:
  (a) detecting or determining the level of expression in the patient of a gene selected from the group consisting of KIBRA and CLSTN2; and
  (b) correlating the level of expression of the gene in the patient with memory performance in the patient.

It should be noted that the methods for detecting or determining the level of expression in the patient of one or more genes of interest are well known in the art. Such methods include, but are not limited to, Northern blotting, which detects specific mRNAs by hybridization.

Another embodiment of the present invention is a method for assessing memory performance in a patient comprising the steps of:
  (c) detecting the presence or absence of a mutation in one or more genes, the genes selected from the group consisting of KIBRA and CLSTN2; and
  (d) correlating the presence or absence of the mutation with memory performance in the patient.

It should be noted that the methods for detecting the presence or absence of a mutation in one or more genes of interest in a patient are well known in the art. Such methods include, but are not limited to, DNA sequencing and restriction fragment length polymorphism (RFLP) analysis.

Yet another embodiment of the present invention is a method for assessing memory performance in a patient comprising the steps of:
  (a) detecting or determining the level of activity in the patient of a gene product of a gene selected from the group consisting of KIBRA and CLSTN2; and
  (b) correlating the level of activity of the gene product in the patient with memory performance.

It should be noted that the methods for detecting or determining the level of activity in a patient of a gene product of one or more genes of interest are well known to a practitioner of ordinary skill in the art. Such methods include, but are not limited to, Western blotting for determining the quantity of expressed gene product by immunoassay.

Another embodiment of the present invention is a method for enhancing memory performance in a subject comprising administering to the subject a compound capable of modulating synaptic plasticity by stimulating the synthesis or activity of a gene product of a gene selected from the group consisting of KIBRA and CLSTN2. Another embodiment of the present invention is a method for enhancing memory performance in a subject comprising administering to the subject a compound capable of modulating synaptic plasticity wherein the compound is a full-length KIBRA protein wherein the DNA sequence encoding the full-length KIBRA protein is (SEQ ID NO: 1)
ATGCCCCGGCCGGAGCTGCCCCTGCCGGAGGGCTGGGAGGAGGCGCGCGA

CTTCGACGGCAAGGTCTACTACATAGACCACAGGAACCGCACCACCAGCT

GGATCGACCCGCGGGACAGGTACACCAAACCGCTCACCTTTGCTGACTGC

ATTAGTGATGAGTTGCCGCTAGGATGGGAAGAGGCATATGACCCACAGGT

TGGAGATTACTTCATAGACCACAACACCAAAACCACTCAGATTGAGGATC

CTCGAGTACAATGGCGGCGGGAGCAGGAACATATGCTGAAGGATTACCTG

GTGGTGGCCCAGGAGGCTCTGAGTGCACAAAAGGAGATCTACCAGGTGAA

GCAGCAGCGCCTGGAGCTTGCACAGCAGGAGTACCAGCAACTGCATGCCG

TCTGGGAGCATAAGCTGGGCTCCCAGGTCAGCTTGGTCTCTGGTTCATCA

TCCAGCTCCAAGTATGACCCTGAGATCCTGAAAGCTGAAATTGCCACTGC

AAAATCCCGGGTCAACAAGCTGAAGAGAGAGATGGTTCACCTCCAGCACG

AGCTGCAGTTCAAAGAGCGTGGCTTTCAGACCCTGAAGAAAATCGATAAG

AAAATGTCTGATGCTCAGGGCAGCTACAAACTGGATGAAGCTCAGGCTGT

CTTGAGAGAAACAAAAGCCATCAAAAAGGCTATTACCTGTGGGGAAAAGG

AAAAGCAAGATCTCATTAAGAGCCTTGCCATGTTGAAGGACGGCTTCCGC

ACTGACAGGGGGTCTCACTCAGACCTGTGGTCCAGCAGCAGCTCTCTGGA

GAGTTCGAGTTTCCCGCTACCGAAACAGTACCTGGATGTGAGCTCCCAGA

CAGACATCTCGGGAAGCTTCGGCATCAACAGCAACAATCAGTTGGCAGAG

AAGGTCAGATTGCGCCTTCGATATGAAGAGGCTAAGAGAAGGATCGCCAA

CCTGAAGATCCAGCTGGCCAAGCTTGACAGTGAGGCCTGGCCTGGGGTGC

TGGACTCAGAGAGGGACCGGCTGATCCTTATCAACGAGAAGGAGGAGCTG

CTGAAGGAGATGCGCTTCATCAGCCCCCGCAAGTGGACCCAGGGGGAGGT

GGAGCAGCTGGAGATGGCCCGGAAGCGGCTGGAAAAGGACCTGCAGGCAG

CCCGGGACACCCAGAGCAAGGCGCTGACGGAGAGGTTAAAGTTAAACAGT

AAGAGGAACCAGCTTGTGAGAGAACTGGAGGAAGCCACCCGGCAGGTGGC

```
AACTCTGCACTCCCAGCTGAAAAGTCTCTCAAGCAGCATGCAGTCCCTGT
CCTCAGGCAGCAGGCCCGGATCCCTCACGTCCAGCCGGGGCTCCCTGGTT
GCATCCAGCCTGGACTCCTCCACTTCAGCCAGCTTCACTGACCTCTACTA
TGACCCCTTTGAGCAGCTGGACTCAGAGCTGCAGAGCAAGGTGGAGTTCC
TGCTCCTGGAGGGGGCCACCGGCTTCCGGCCCTCAGGCTGCATCACCACG
ATCCACGAGGATGAGGTGGCCAAGACCCAGAAGGCAGAGGGAGGTGGCCG
CCTGCAGGCTCTGCGTTCCCTGTCTGGCACCCCAAAGTCCATGACCTCCC
TATCCCCACGTTCCTCTCTCCTCCCCCTCCCCACCCTGTTCCCCTCTC
ATGGCTGACCCCCTCCTGGCTGGTGATGCCTTCCTCAACTCCTTGGAGTT
TGAAGACCCGGAGCTGAGTGCCACTCTTTGTGAACTGAGCCTTGGTAACA
GCGCCCAGGAAAGATACCGGCTGGAGGAACCAGGAACGGAGGGCAAGCAG
CTGGGCCAAGCTGTGAATACGGCCCAGGGGTGTGGCCTGAAAGTGGCCTG
TGTCTCAGCCGCCGTATCGGACGAGTCAGTGGCTGGAGACAGTGGTGTGT
ACGAGGCTTCCGTGCAGAGACTGGGTGCTTCAGAAGCTGCTGCATTTGAC
AGTGACGAATCGGAAGCAGTGGGTGCGACCCGAATTGAGATTGCCCTGAA
GTATGATGAGAAGAATAAGCAATTTGCAATATTAATCATCCAGCTGAGTA
ACCTTTCTGCTCTGTTGCAGCAACAAGACCAGAAAGTGAATATCCGCGTG
GCTGTCCTTCCTTGCTCTGAAAGCACAACCTGCCTGTTCCGGACCCGGCC
TCTGGACGCCTCAGACACTCTAGTGTTCAATGAGGTGTTCTGGGTATCCA
TGTCCTATCCAGCCCTTCACCAGAAGACCTTAAGAGTCGATGTCTGTACC
ACCGACAGGAGCCATCTGGAAGAGTGCCTGGGAGGCGCCCAGATCAGCCT
GGCGGAGGTCTGCCGGTCTGGGGAGAGGTCGACTCGCTGGTACAACCTTC
TCAGCTACAAATACTTGAAGAAACAGAGCAGGGAGCTCAAGCCAGTGGGA
GTCATGGCCCCTGCCTCAGGGCCTGCCAGCACGGACGCTGTGTCTGCTCT
GTTGGAACAGACAGCAGTGGAGCTGGAGAAGAGGCAGGAGGGCAGGAGCA
GCACACAGACACTGGAAGACAGCTGGAGGTATGAGGAGACCAGTGAGAAT
GAGGCAGTAGCCGAGGAAGAGGAGGAGGAGGTGGAGGAGGAGGAGGGAGA
AGAGGATGTTTTCACCGAGAAAGCCTCACCTGATATGGATGGGTACCCAG
CATTAAAGGTGGACAAAGAGACCAACACGGAGACCCCGGCCCCATCCCCC
ACAGTGGTGCGACCTAAGGACCGGAGAGTGGGCACCCCGTCCCAGGGGCC
ATTTCTTCGAGGGAGCACCATCATCCGCTCTAAGACCTTCTCCCCAGGAC
CCCAGAGCCAGTACGTGTGCCGGCTGAATCGGAGTGATAGTGACAGCTCC
ACTCTGTCCAAAAAGCCACCTTTTGTTCGAAACTCCCTGGAGCGACGCAG
CGTCCGGATGAAGCGGCCTTCCTCGGTCAAGTCGCTGCGCTCCGAGCGTC
TGATCCGTACCTGGCTGGACCTGGAGTTAGACCTGCAGGCGACAAGAACC
TGGCACAGCCAATTGACCCAGGAGATCTCGGTGCTGAAGGAGCTCAAGGA
GCAGCTGGAACAAGCCAAGAGCCACGGGGAGAAGGAGCTGCCACAGTGGT
TGCGTGAGGACGAGCGTTTCCGCCTGCTGCTGAGGATGCTGGAGAAGCGG
CAGATGGACCGAGCGGAGCACAAGGGTGAGCTTCAGACAGACAAGATGAT
GAGGGCAGCTGCCAAGGATGTGCACAGGCTCCGAGGCCAGAGCTGTAAGG
AACCCCCAGAAGTTCAGTCTTTCAGGGAGAAGATGGCATTTTTCACCCGG
CCTCGGATGAATATCCCAGCTCTCTCTGCAGATGACGTCTAA.
```

Another embodiment of the present invention is a method for enhancing memory performance in a subject comprising administering to the subject a compound capable of modulating synaptic plasticity wherein the compound is a full-length KIBRA protein comprising the following protein sequence

```
                                              (SEQ ID NO: 3)
MPRPELPLPEGWEEARDFDGKVYYIDHTNRTTSWIDPRDRYTKPLTFADC
LSDELPLGWEEAYDPQVGDYFIDHNTKTTQIEDPRVQWRREQEHMLKDYL
VVAQEALSAQKEIYQVKQQRLELAQQEYQQLHAVWEHKLGSQVSLVSGSS
SSSKYDPEILKAEIATAKSRVNKLKREMVHLQHELQFKERGFQTLKKIDK
KMSDAQGSYKLDEAQAVLRETKAIKKAITCGEKEKQDLIKSLAMLKDGFR
TDRGSHSDLWSSSSSLESSSFPLPKQYLDVSSQTDISGSFGINSNNQLAE
KVRLRLRYEEAKRRIANLKIQLAKLDSEAWPGVLDSERDRLILINEKEEL
LKEMRFISPRKWTQGEVEQLEMARKRLEKDLQAARDTQSKALTERLKLNS
KRNQLVRELEEATRQVATLHSQLKSLSSSMQSLSSGSSPGSLTSSRGSLV
ASSLDSSTSASFTDLYYDPFEQLDSELQSKVEFLLLEGATGFRPSGCITT
IHEDEVAKTQKAEGGGRLQALRSLSGTPKSMTSLSPRSSLSSPSPPCSPL
MADPLLAGDAFLNSLEFEDPELSATLCELSLGNSAQERYRLEEPGTEGKQ
LGQAVNTAQGCGLKVACVSAAVSDESVAGDSGVYEASVQRLGASEAAAFD
SDESEAVGATRIQIALKYDEKNKQFAILIIQLSNLSALLQQQDQKVNIRV
AVLPCSESTTCLFRTRPLDASDTLVFNEVFWVSMSYPALHQKTLRVDVCT
TDRSHLEECLGGAQISLAEVCRSGERSTRWYNLLSYKYLKKQSRELKPVG
VMAPASGPASTDAVSALLEQTAVELEKRQEGRSSTQTLEDSWRYEETSEN
EAVAEEEEEVEEEEGEEDVFTEKASPDMDGYPALKVDKETNTETPAPSP
TVVRPKDRRVGTPSQGPFLRGSTIIRSKTFSPGPQSQYVCRLNRSDSDSS
TLSKKPPFVRNSLERRSVRMKRPSSVKSLRSERLIRTSLDLELDLQATRT
WHSQLTQEISVLKELKEQLEQAKSHGEKELPQWLREDERFRLLLRMLEKR
QMDRAEHKGELQTDKMMRAAAKDVHRLRGQSCKEPPEVQSFREKMAFFTR
PRMNIPALSADDV.
```

Another embodiment of the present invention is a method for enhancing memory performance in a subject comprising administering to the subject a compound capable of modulating synaptic plasticity wherein the compound is a truncated KIBRA protein wherein the DNA sequence encoding the truncated KIBRA protein is

```
                                              (SEQ ID NO: 2)
AAAAAGGCTATTACCTGTGGGGAAAAGGAAAAGCAAGATCTCATTAAGAG
CCTTGCCATGTTGAAGGACGGCTTCCGCACTGACAGGGGGTCTCACTCAG
ACCTGTGGTCCAGCAGCAGCTCTCTGGAGAGTTCGAGTTTCCCGCTACCG
AAACAGTACCTGGATGTGAGCTCCCAGACAGACATCTCGGGAAGCTTCGG
CATCAACAGCAACAATCAGTTGGCAGAGAAGGTCAGATTGCGCCTTCGAT
```

```
ATGAAGAGGCTAAGAGAAGGATCGCCAACCTGAAGATCCAGCTGGCCAAG

CTTGACAGTGAGGCCTGGCCTGGGGTGCTGGACTCAGAGAGGGACCGGCT

GATCCTTATCAACGAGAAGGAGGAGCTGCTGAAGGAGATGCGCTTCATCA

GCCCCCGCAAGTGGACCCAGGGGGAGGTGGAGCAGCTGGAGATGGCCCGG

AAGCGGCTGGAAAAGGACCTGCAGGCAGCCCGGGACACCCAGAGCAAGGC

GCTGACGGAGAGGTTAAAGTTAAACAGTAAGAGGAACCAGCTTGTGAGAG

AACTGGAGGAAGCCACCCGGCAGGTGGCAACTCTGCACTCCCAGCTGAAA

AGTCTCTCAAGCAGCATGCAGTCCCTGTCCTGAGGCAGCAGCCCCGGATC

CCTCACGTCCAGCCGGGGCTCCCTGGTTGCATCCAGCCTGGACTCCTCCA

CTTCAGCCAGCTTCACTGACCTCTACTATGACCCCTTTGAGCAGCTGGAC

TCAGAGCTGCAGAGCAAGGTGGAGTTCCTGCTCCTGGAGGGGGCCACCGG

CTTCCGGCCCTCAGGCTGCATCACCACCATCCACGAGGATGAGGTGGCCA

AGACCCAGAAGGCAGAGGGAGGTGGCCGCCTGCAGGCTCTGCGTTCCCTG

TCTGGCACCCCAAAGTCCATGACCTCCCTATCCCCACGTTCCTCTCTCTC

CTCCCCCTCCCCACCCTGTTGCCCTCTCATGGCTGACCCCCTCCTGGCTG

GTGATGCCTTCCTCAACTCCTTGGAGTTTGAAGACCCGGAGCTGAGTGCC

ACTCTTTGTGAACTGAGCCTTGGTAACAGCGCCCAGGAAAGATACCGGCT

GGAGGAACCAGGAACGGAGGGCAAGCAGCTGGGCCAAGCTGTGAATACGG

CCCAGGGGTGTGGCCTGAAAGTGGCCTGTGTCTCAGCCGCCGTATCGGAC

GAGTCAGTGGCTGGAGAGAGTGGTGTGTACGAGGCTTCCGTGCAGAGACT

GGGTGCTTCAGAAGCTGCTGCATTTGACAGTGACGAATCGGAAGCAGTGG

GTGCGACCCGAATTCAGATTGCCCTGAAGTATGATGAGAAGAATAAGCAA

TTTGCAATATTAATCATCCAGCTGAGTAACCTTTCTGCTCTGTTGCAGCA

ACAAGACCAGAAAGTGAATATCCGCGTGGCTGTCCTTCCTTGCTCTGAAA

GCACAACCTGCCTGTTCCGGACCCGGCCTCTGGACGCCTCAGACACTCTA

GTGTTCAATGAGGTGTTCTGGGTATCCATGTCCTATCCAGCCCTTCACCA

GAAGACCTTAAGAGTCGATGTCTGTACCACCGACAGGAGCCATCTGGAAG

AGTGCCTGGGAGGCGCCCAGATCAGCCTGGCGGAGGTCTGCCGGTCTGGG

GAGAGGTCGAGTCGCTGGTACAACCTTCTCAGCTACAAATACTTGAAGAA

ACAGAGCAGGGAGCTCAAGCCAGTGGGAGTCATGGCCCCTGCCTCAGGGC

CTGCCAGCACGGACGCTGTGTCTGCTCTGTTGGAACAGACAGCAGTGGAG

CTGGAGAAGAGGCAGGAGGGCAGGAGCAGCACACAGACACTGGAAGACAG

CTGGAGGTATGAGGAGACCAGTGAGAATGAGGCAGTAGCCGAGGAAGAGG

AGGAGGAGGTGGAGGAGGAGGAGGGGAGAAGAGGATGTTTTCACCGAGAAA

GCCTCACCTGATATGGATGGGTACCCAGCATTAAAGGTGGACAAAGAGAC

CAACACGGAGACCCCGGCCGCATCCCCCACAGTGGTGCGACCTAAGGACC

GGGAGAGTGGGCACCCCGTCCCAGGGGCCATTTCTTCGAGGGAGCACCATC

ATCCGCTCTAAGACCTTCTCCCCAGGACCCCAGAGCCAGTACGTGTGCCG

GCTGAATCGGAGTGATAGTGACAGCTCCACTCTGTCCAAAAAGCCACCTT

TTGTTCGAAACTCCCTGGAGCGACGCAGCGTCCGGATGAAGCGGCCTTCC

TCGGTCAAGTCGCTGCGCTCCGAGCGTCTGATCCGTACCTCGCTGGACCT

GGAGTTAGACCTGCAGGCGACAAGAACCTGGCACAGCCAATTGACCCAGG

AGATCTCGGTGCTGAAGGAGCTCAAGGAGCAGCTGGAACAAGCCAAGAGC

CACGGGGAGAAGGAGCTGCCACAGTGGTTGCGTGAGGACGAGCGTTTCCG

CCTGCTGCTGAGGATGCTGGAGAAGCGGCAGATGGACCGAGCGGAGCACA

AGGGTGAGCTTCAGACAGACAAGATGATGAGGGCAGCTGCCAAGGATGTG

CACAGGCTCCGAGGCCAGAGCTGTAAGGAACCCCCAGAAGTTCAGTCTTT

CAGGGAGAAGATGGCATTTTTCACCCGGCCTCGGATGAATATCCCAGCTC

TCTCTGCAGATGACGTCTAA.
```

Another embodiment of the present invention is a method for enhancing memory performance in a subject comprising administering to the subject a compound capable of modulating synaptic plasticity wherein the compound is a truncated KIBRA protein comprising the following protein sequence (SEQ ID NO: 4)
KKAITCGEKEKQDLIKSLAMLKDGFRTDRGSHSDLWSSSSSLESSSFPLP
KQYLDVSSQTDISGSFGINSNNQLAEKVRLRLRYEEAKRRIANLKIQLAK
LDSEAWPGVLDSERDRLILINEKEELLKEMRFISPRKWTQGEVEQLEMAR
KRLEKDLQAARDTQSKALTERLKLNSKRNQLVRELEEATRQVATLHSQLK
SLSSSMQSLSSGSSPGSLTSSRGSLVASSLDSSTSASFTDLYYDPFEQLD
SELQSKVEFLLLEGATGFRPSGCITTIHEDEVAKTQKAEGGGRLQALRSL
SGTPKSMTSLSPRSSLSSPSPPCSPLMADPLLAGDAFLNSLEFEDPELSA
TLCELSLGNSAQERYRLEEPGTEGKQLGQAVNTAQGCGLKVACVSAAVSD
ESVAGDSGVYEASVQRLGASEAAAFDSDESEAVGATRIQIALKYDEKNKQ
FAILIIQLSNLSALLQQQDQKVNIRVAVLPCSESTTCLFRTRPLDASDTL
VFNEVFWVSMSYPALHQKTLRVDVCTTDRSHLEECLGGAQISLAEVCRSG
ERSTRWYNLLSYKYLKKQSRELKPVGVMAPASGPASTDAVSALLEQTAVE
LEKRQEGRSSTQTLEDSWRYEETSENEAVAEEEEEEVEEEEGEEDVFTEK
ASPDMDGYPALKVDKETNTETPAPSPTVVRPKDRRVGTPSQGPFLRGSTI
IRSKTFSPGPQSQYVCRLNRSDSDSSTLSKKPPFVRNSLERRSVRMKRPS
SVKSLRSERLIRTSLDLELDLQATRTWHSQLTQEISVLKELKEQLEQAKS
HGEKELPQWLREDERFRLLLRMLEKRMDRAEHKGELQTDKMMRAAAKDVH
RLRGQSCKEPPEVQSFREKMAFFTRPRMNIPALSADDV.

Yet another embodiment of the present invention is a method for evaluating the ability of a compound to affect the expression of a full-length KIBRA protein (SEQ ID NO: 3) in hippocampus of a subject which comprises the steps of:
 (a) administering the compound to the subject
 (b) measuring the amount of expression of full-length KIBRA protein in hippocampus of the subject.

Another embodiment of the present invention is a method for evaluating the ability of a compound to affect the expression of a truncated KIBRA protein (SEQ ID NO: 4), wherein the truncated KIBRA protein is lacking the amino-terminal 223 amino acids of the full-length KIBRA protein in hippocampus of a subject which comprises the steps of:
 (a) administering the compound to a subject
 (b) measuring the amount of expression of truncated KIBRA protein in hippocampus of the subject; and (c) comparing the amount in step (b) with the amount of expression of truncated KIBRA protein in hippocampus of the subject.

Another embodiment of the present invention is a method of treating a subject with an episodic memory defect due to the existence of a disease or condition affecting episodic memory, which comprises administering to the subject a compound capable of enhancing episodic memory, the compound being selected from the group selected from:

(a) truncated KIBRA protein (SEQ ID NO: 4);

(b) a nucleic acid molecule encoding truncated KIBRA protein (SEQ ID NO: 4; and (c) a compound stimulating the synthesis or activity of truncated KIBRA protein;

in a quantity effective to enhance episodic memory to thereby treat the subject's episodic memory defect.

It should be noted that the effective quantity or range of effective quantities of a compound capable of enhancing episodic memory would be well known to a practitioner of an ordinary skill in the art.

Yet another embodiment of the present invention is an isolated and purified protein that is a truncated KIBRA protein derived from the sequence of full-length KIBRA protein (SEQ ID NO: 2), wherein the protein is truncated by the elimination of a portion of the amino-terminal region of the protein such that a number of amino acids from about 100 amino acids to about 300 amino acids beginning at the amino-terminus of the protein are removed and wherein the protein retains a C2-like domain, a glutamic acid-rich stretch and a protein kinase C (PKC)ξ-interacting domain of the full-length protein.

Another embodiment of the present invention is a method of enhancing or modulating memory function in a subject comprising the step of administering to the subject a quantity of a composition containing KIBRA rs17070145 SNP effective to enhance or modulate the memory function in the subject.

Another embodiment of the present invention is method of enhancing or modulating memory function in a subject comprising the step of administering to the subject a quantity of a composition containing CLSTN2 rs6439886 SNP effective to enhance or modulate the memory function in the subject.

KIBRA Protein

In the present invention, novel memory-related functions of the KIBRA gene were identified. KIBRA is a cytoplasmic protein that is highly expressed in human kidney and brain and represents a new member of the family of signal transducer neuronal proteins. (J. Kremerskothen et al., *Biochem. Biophys. Res. Commun.* 300, 862 (2003)).

In the present invention, studies have shown that KIBRA alleles were strongly associated with differential memory performance in two distinct, healthy populations. This fact suggests that KIBRA alleles affect memory performance in humans independent of ethnicity, age, language and type of the particular memory task used to assess level of memory performance. It is further suggested that KIBRA alleles affect memory performance in humans by modulating synaptic plasticity. Importantly, the acquisition and consolidation of memory are thought to depend on synaptic plasticity. (Y. Dudai, *Curr. Opin. Neurobiol.* 12, 211 (2002)).

Full-length KIBRA comprises 1113 amino acids (aa). A truncated form, which was found to be expressed in the hippocampus, lacks the first 223 aa and contains a C2-like domain, a glutamic acid-rich stretch and a protein kinase C (PKC)ξ-interacting domain. (K. Buther, C. Plaas, A. Barnekow, J. Kremerskothen, *Biochem. Biophys. Res. Commun.* 317, 703 (2004)).

It was previously established that PKCξ is involved in memory formation and in the consolidation of long-term potentiation. (E. A. Drier et al., *Nat. Neurosci.* 5, 316 (2002); T. C. Sacktor et al., *Proc. Natl. Acad. Sci. U.S. A* 90, 8342 (1993)). The C2-like domain of KIBRA, which likely mediates $Ca^{2+}$ sensitivity (J. Rizo, T. C. Sudhof, *J. Biol. Chem.* 273, 15879 (1998)), is similar to the C2 domain of synaptotagmin, which is believed to function as the main $Ca^{2+}$ sensor in synaptic vesicle exocytosis. (J. Kremerskothen et al., *Biochem. Biophys. Res. Commun.* 300, 862 (2003); J. Ubach, X. Zhang, X. Shao, T. C. Sudhof, J. Rizo, *EMBO J.* 17, 3921 (1998)). Importantly, the memory-associated KIBRA haplotype block and the memory-associated KIBRA SNP described below map within the truncated KIBRA, which contains both the C2-like and the PKCξ-interacting domains.

Taken together, converging evidence from independent experiments in the present study indicates a major role of KIBRA in normal human memory performance.

Therefore, one embodiment of the present invention is a method of enhancing memory function in a subject, which comprises administering to the subject a compound capable of modulating synaptic plasticity in a subject in an amount effective to enhance the subject's memory function.

Another embodiment of the present invention is a method of enhancing memory function in a subject, which comprises administering to the subject a compound containing KIBRA protein in an amount effective to enhance the subject's memory function.

KIBRA Memory-Related SNPs

The present invention also features KIBRA memory-related SNPs such as the rs17070145 single nucleotide polymorphism. KIBRA SNP rs17070145 is a common T→C substitution within the ninth intron of KIBRA (encoding the neuronal protein KIBRA). According to the experiments performed in the course of the present invention, carriers of the KIBRA rs17070145 SNP demonstrated superior memory performance than non-carriers.

One embodiment of the present invention is a method of using the KIBRA rs17070145 SNP taught by the present invention to modulate human memory function.

Another embodiment of the present invention is a method of enhancing memory function in a subject, which comprises administering to the subject a compound containing KIBRA rs17070145 SNP in an amount effective to enhance the subject's memory function.

These methods of enhancing or modulating memory function can be carried out by administering a nucleic acid encoding KIBRA rs17070145 SNP or by administering the protein encoded by KIBRA rs17070145 SNP. Typically, the composition including the nucleic acid or protein for administration is administered by a route selected from the group consisting of intralesional delivery; intramuscular injection; intravenous injection; infusion; liposome mediated delivery; viral infection; gene bombardment; topical delivery; nasal delivery; oral delivery; anal delivery; ocular delivery; cerebrospinal delivery; and otic delivery. Analogous methods can be used with other SNPs as described herein.

Yet another embodiment of the present invention is a method of using the KIBRA rs11738934 SNP (FIG. 3, SNP 4) taught by the present invention to modulate human memory function.

Another embodiment of the present invention is a method of enhancing memory function in a subject, which comprises administering to the subject a compound containing KIBRA rs11738934 SNP in an amount effective to enhance the subject's memory function.

Yet another embodiment of the present invention is a method of using the KIBRA rs6862868 SNP (FIG. 3, SNP 5) taught by the present invention to modulate human memory function.

Another embodiment of the present invention is a method of enhancing memory function in a subject, which comprises administering to the subject a compound containing KIBRA rs6862868 SNP in an amount effective to enhance the subject's memory function.

Yet another embodiment of the present invention is a method of using the KIBRA rs2241368 SNP (FIG. 3, SNP 6) taught by the present invention to modulate human memory function.

Another embodiment of the present invention is a method of enhancing memory function in a subject, which comprises administering to the subject a compound containing KIBRA rs2241368 SNP in an amount effective to enhance the subject's memory function.

Yet another embodiment of the present invention is a method of using the KIBRA rs17551608 SNP (FIG. 3, SNP 7) taught by the present invention to modulate human memory function.

Another embodiment of the present invention is a method of enhancing memory function in a subject, which comprises administering to the subject a compound containing KIBRA rs17551608 SNP in an amount effective to modulate human memory function.

Yet another embodiment of the present invention is a method of using the KIBRA rs4976606 SNP (FIG. 3, SNP 9) taught by the present invention to modulate human memory function.

Another embodiment of the present invention is a method of enhancing memory function in a subject, which comprises administering to the subject a compound containing KIBRA rs4976606 SNP in an amount effective to modulate human memory function.

Yet another embodiment of the present invention is a method of using the KIBRA rs3822660 SNP (FIG. 3, SNP 10) taught by the present invention to modulate human memory function.

Another embodiment of the present invention is a method of enhancing memory function in a subject, which comprises administering to the subject a compound containing KIBRA rs3822660 SNP in an amount effective to modulate human memory function.

Yet another embodiment of the present invention is a method of using the KIBRA rs3822659 SNP (FIG. 3, SNP 11) taught by the present invention to modulate human memory function.

Another embodiment of the present invention is a method of enhancing memory function in a subject, which comprises administering to the subject a compound containing KIBRA rs3822659 SNP in an amount effective to modulate human memory function.

Yet another embodiment of the present invention is a method of using the KIBRA rs3733980 SNP (FIG. 3, SNP 12) taught by the present invention to modulate human memory function.

Another embodiment of the present invention is a method of enhancing memory function in a subject, which comprises administering to the subject a compound containing KIBRA rs3733980 SNP in an amount effective to modulate human memory function.

Yet another embodiment of the present invention is a method of using a haplotype located between SNP 4 (rs11738934) and SNP 12 (rs3733980), such that the genetic distance between these SNPs is 51032 base pairs, taught by the present invention, to modulate memory function.

Still another embodiment of the present invention is a method of enhancing memory function in a subject, which comprises administering to the subject a compound containing a haplotype located between SNP 4 (rs11738934) and SNP 12 (rs3733980), such that the genetic distance between these SNPs is 51032 base pails in an amount effective to modulate human memory function.

These methods of enhancing or modulating memory function can be carried out by administering a nucleic acid containing the haplotype located between SNP 4 (rs11738934) and SNP 12 (rs3733980). Typically, the composition including the nucleic acid for administration is administered by a route selected from the group consisting of intralesional delivery; intramuscular injection; intravenous injection; infusion; liposome mediated delivery; viral infection; gene bombardment; topical delivery; nasal delivery; oral delivery; anal delivery; ocular delivery; cerebrospinal delivery; and otic delivery.

With regard to the above embodiments, it is further noted that an amount effective to modulate human memory function will be known to a practitioner of reasonable skill in the art. Similarly, an amount effective to enhance human memory function will also be known to a practitioner of reasonable skill in the art.

Methods of administering nucleic acids, sometimes referred to as "gene therapy" are generally known in the art and are described in T. Strachan & A. P. Read, "Human Molecular Genetics" (2d ed., Wiley-Liss, New York, 1999), pp. 515-543, incorporated herein by this reference.

The KIBRA gene, transcripts (full length and truncated), polypeptides (full length and truncated), all alleles (including both the T and the C allele defined by rs17070145) and all SNPs in the KIBRA locus (including rs17070145), which are associated with memory, are useful diagnosis and pharmacogenetic applications. KIBRA is a disease-severity modifier for normal age-related memory loss and amnestic disorders. Amnestic disorders include but are not limited to Alzheimer's disease; traumatic brain injury; brain injury caused by therapeutic agents, drug use, environmental conditions, cancer or other pathological conditions such as infectious disease; epilepsy; learning disabilities; mental retardation (e.g., fragile X syndrome); Down syndrome; schizophrenia; depression; mild cognitive impairment (MCI); Parkinson's disease; stroke-induced loss of function; cerebral microangiopathy; and chemo-brain (difficulties with memory, attention and other cognitive functions that patients may suffer during and after chemotherapy). Diagnostic applications therefore include evaluation of disease susceptibility, prognosis, and monitoring of disease or treatment process. KIBRA nucleic acid, protein and SNPs can be used for facilitating the design and development of various molecular diagnostic tools (e.g., GeneChips™ containing probe sets, in vivo diagnostic probes, PCR primers, antibodies, kits, etc.). In vivo imaging can be used for diagnosis, using fMRI or agents that detect KIBRA. Mass spectroscopy can also be used to detect KIBRA protein and alleles.

Pharmacogenetic applications include providing individualized medicine via predictive drug profiling systems, e.g., by correlating specific genomic motifs with the clinical response of a patient to individual drugs, e.g., for therapeutic decision-making and for selection of patients for clinical trials. In particular, genotyping and stratification based on KIBRA T or C haplotype (defined in the rs17070145 SNP) is useful for therapy or clinical trials with agents designed to treat normal age-related or amnestic disorders.

In addition, the present invention is useful for multiplex SNP and haplotype profiling, including but not limited to the identification of therapeutic, diagnostic, and pharmacogenetic targets at the gene, mRNA, protein, and pathway level. Profiling of splice variants and deletions/truncations is also useful for diagnostic and therapeutic applications.

The KIBRA gene, transcripts, SNPs, alleles and polypeptides, described herein, are also useful as drug targets for the development of therapeutic drugs for the treatment of normal age-related memory loss and amnestic disorders, and for enhancement of normal memory. A variety of known methods may be used to identify such compounds. The compounds can be small molecules, peptides, peptidomimetics, antisense molecules, siRNA, etc. Compounds that affect the activity, expression, translation, processing, transport, and degradation of KIBRA are useful as therapeutics.

With regard to the above embodiments, it is further noted that an amount effective to modulate human memory function will be known to a practitioner of reasonable skill in the art. Similarly, an amount effective to enhance human memory function will also be known to a practitioner of reasonable skill in the art.

Calsyntenin 2 Protein

In the present invention, novel memory-related functions of the Calsyntenin 2 gene ("CLSTN2") were identified. CLSTN2 is a neuronal protein located in the postsynaptic membrane of excitatory synapses. (G. Hintsch et al. Mol. and Cell. Neuro. 21, 403 (2002)).

In particular, CLSTN2 rs6439886 SNP, representing a common T→C substitution within the first intron of CLSTN2 (encoding the neuronal protein Calsyntenin 2) was shown to be strongly affiliated with memory performance in humans. Carriers of the CLSTN2 rs6439886 SNP demonstrated superior memory performance than non-carriers.

One embodiment of the present invention is a method of using the CLSTN2 rs6439886 SNP taught by the present invention to modulate human memory function.

Another embodiment of the present invention is a method of enhancing memory function in a subject, which comprises administering to the subject a compound containing CLSTN2 rs6439886 SNP in an amount effective to enhance the subject's memory function.

With regard to the above embodiments, it is further noted that an amount effective to modulate human memory function will be known to a practitioner of reasonable skill in the art. Similarly, an amount effective to enhance human memory function will also be known to a practitioner of reasonable skill in the art.

Pharmaceutical Formulations and Modes of Administration

The particular compound that affects the disorders or conditions of interest can be administered to a patient either by itself or in pharmaceutical compositions where it is mixed with suitable carriers or excipient(s). In treating a patient exhibiting a disorder of interest, a therapeutically effective amount of an agent or agents such as these is administered. A therapeutically effective dose refers to that amount of the compound that results in amelioration of symptoms or a prolongation of survival in a patient.

The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. In addition, the molecules tested can be used to determine the structural features that enable them to act on the ob gene control region, and thus to select molecules useful in this invention. Those skilled in the art will know how to design drugs from lead molecules, using techniques well known in the art.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known. e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Some methods of delivery that may be used include:
a. encapsulation in liposomes,
b. transduction by retroviral vectors,
c. localization to nuclear compartment utilizing nuclear targeting site found on most nuclear proteins,
d. transfection of cells ex vivo with subsequent reimplantation or administration of the transfected cells,
e. a DNA transporter system.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

EXAMPLES

Example 1

Whole-genome Scan in the Swiss Sample.

351 young adults (22.9±4.1 years of age) from Switzerland were recruited. Genetic association studies in outbred populations such as the present one may be prone to false-positivity because non-random genetic heterogeneity within the study sample (i.e. population structure) can lead to spurious associations between a genetic marker and a phenotype (9). We therefore performed a structured association analysis (10) and found that the allele-frequency divergence in this population was moderate and that the participants' genetic backgrounds formed one normally distributed cluster (P=0.6, see methods). Only ten subjects were identified as outliers (i.e. probability of cluster allocation lower than 25%) and were therefore excluded from the genetic association studies. The remaining population (n=341) was stratified into 4 groups according to their performance in a verbal memory task. These quartiles were genotyped at 502,627 SNPs. Poor performing SNPs were cropped, and both single-point and sliding window (multi-point) statistical approaches were employed to select SNPs associated with performance at high statistical confidence. Two SNPs were significant with both analysis strategies: rs17070145 and rs6439886. Interestingly, both SNPs map within genes expressed in the human brain: rs17070145 is a common T→C substitution within the ninth intron of KIBRA (encoding the neuronal protein KIBRA), rs6439886 is a common T→C substitution within the first intron of CLSTN2 (encoding the synaptic protein calsyntenin 2).

Materials and Methods.

Memory testing and genotyping were performed in 351 healthy young Swiss subjects (240 females, 111 males; mean age 22.8±0.2 [standard error] years). After complete description of the study to the subjects, written informed consent was obtained. The ethics committee of the Canton of Zurich, Switzerland approved the study protocol. Memory capacity was tested during two consecutive days. On the first day, subjects viewed 6 series of 5 semantically unrelated nouns presented at a rate of 1 word per s with the instruction to learn the words for immediate free recall after each series. In addition, subjects underwent an unexpected delayed free-recall test of the learned words after 5 min and again after 24 h. Both delayed recall tests reflect episodic memory (11). In contrast to the 5-min recall, the 24-h recall additionally requires long-term synaptic changes (29).

Structured Association Analysis

Structured association analysis was performed by individually genotyping all 351 Swiss subjects at 318 unlinked SNPs. Calculation of population structure was done by the STRUCTURE program following the developers' instructions (10). We estimated the ancestry of study subjects under the a priori assumption of K=2 discrete subpopulations. Structured association analysis revealed moderate allele-frequency divergence among populations. Identical results were obtained under the a priori assumption of 3=K=6 discrete subpopulations.

Affymetrix 500K GeneChip SNP Genotyping in Training Cohort

Individual genomic DNA concentrations of the 351 subjects were determined using the Quant-iT™ PicoGreen® dsDNA Assay Kit (Invitrogen, Carlsbad, Calif.) according to the manufacturer's instructions. Individuals were designated to each pool based on their quartile ranking in performance on the verbal episodic memory task. Groupings were based on 5-min free recall performance (i.e. bottom 25%, bottom 50%, top 50%, and top 25% performers). Each individual contributed a total of 120 ng of DNA to the pool and each pool was created de novo a total of three times. These three pools were then genotyped in duplicate on both the Nsp I and Sty I Early Access 500K Mendel array from Affymetrix (Santa Clara, Calif.). Pools were composed as follows, bottom 25% (90 individuals, mean genomic DNA concentration of 100.6 ng/µl), bottom 50% (171 individuals, mean concentration of 97.1 ng/µl), top 50% (180 individuals, mean concentration of 95.1 ng/µl), top 25% (136 individuals, mean concentration of 95.4 ng/µl). Once created, each pool was diluted to 50 ng/µl with reduced TE buffer in preparation for genotyping.

Array-based SNP Genotyping

Samples were processed as described in the Early Access version 2.0 of the Mendel Array protocol (Affymetrix). Briefly, quality and relative concentrations of the pools and their replicates were assayed on 2% TAE agarose gel. 250 ng (5 µl) of DNA from each pool and replicates was digested in parallel with 10 units of Nsp I and Sty I restriction enzymes (New England Biolabs, Beverly, Mass.) for 2 hours at 37° C. Enzyme specific adaptor oligonucleotides were then ligated onto the digested ends with T4 DNA Ligase for three hours at 16° C. After dilution with water, 5 µl of the diluted ligation reactions were subjected to PCR. PCR was performed using Titanium Taq DNA Polymerase (BD Biosciences, San Jose, Calif.) in the presence of 25 µM PCR primer 002 (Affymetrix), 350 µM each dNTP, 1M Betaine (USB, Cleveland, Ohio), and 1× Titanium Taq PCR Buffer (BD Biosciences). Cycling parameters were as follows, initial denaturation at 94° C. for 3 minutes, amplification at 94° C. for 30 seconds, 60° C. for 30 seconds and extension at 68° C. for 15 seconds repeated a total of 30 times, final extension at 68° C. for 7 minutes. PCR products from three reactions were combined and purified using the MinElute 96-well UF PCR purification plates (Qiagen, Valencia, Calif.) according to the manufacturer's directions. Samples were collected into microfuge tubes and spun at 16,000×g for 10 minutes. The purified product was recovered from the tube taking special care not to disturb the white gel-like pellet of magnesium phosphate. PCR products were then verified to migrate at an average size between 200-800 bps using 2% TAE gel electrophoresis. Sixty micrograms of purified PCR products were then fragmented using 0.25 units of DNAse I at 37° C. for 35 minutes. Complete fragmentation of the products to an average size less than 180 bps was verified using 2% TAE gel electrophoresis. Following fragmentation, the DNA was end labeled using 105 units of terminal deoxynucleotidyl transferase at 37° C. for 2 hours. The labeled DNA was then hybridized onto the respective Mendel array at 49° C. for 18 hours at 60 rpm. The hybridized array was washed, stained, and scanned according to the manufacturer's (Affymetrix) instructions.

Statistical Analysis

Calculation of a SNP's allelic frequency was based on the corresponding Relative Allele Signal (RAS) score, which provides a quantitative index of allele frequencies in pooled DNA (30). Generally, RAS=A/(A+B), whereby A refers to the median match/mismatched differences of the major allele and B for the minor allele (Affymetrix Technical Manual). Since both sense and antisense directions are probed, there are two RAS values. RAS1 (sense) and RAS2 (antisense). Because RAS1 and RAS2 are independent predictions of allelic frequency with distinct variability we treated both values as independent experiments. To generate RAS values from the Affymetrix software for the GeneChip.RTM. Human Mapping 500K arrays we developed a PERL script which is freely available on the following website of the Translational Genomics Research Institute, Phoenix, Ariz.: (bioinformatics.tgen.org/software/tgen-array/).

Two different and stringent statistical approaches were combined to select SNPs of high statistical confidence. Only those SNPs meeting the criteria of both approaches were selected for subsequent individual genotyping. In order to pick out significant physically contiguous clusters of SNPs, a genome-wide windowing approach was employed. RAS scores were generated by the Perl script described above followed by a student's t-test comparing RAS1 and RAS2 separately across all ~500,000 SNPs for the top 25% vs. the bottom 25% performers and the top 50% vs. the bottom 50% performers in the Swiss population. Next a median t-test score at sliding window sizes of 3, 5, 10, 20, and 40 SNPs for both RAS1 and RAS2 across the entire genome was calculated and graphed to identify significant groupings of SNPs at various window sizes.

The second statistical method focused on identifying statistically significant individual SNPs rather than clusters of SNPs. RAS-derived allelic frequencies were used to calculate SNP specific $\chi^2$-values for following comparisons: top 50% vs. bottom 50% performers (entire sample) and top 25% vs. bottom 25% performers (distribution extremes). Because RAS I and RAS2 values were treated independently, statistics for each SNP were calculated a total of 4 times. SNPs fulfilling following criteria in at least one of the four comparisons were considered significant with this method: $\chi^2=28$, df=1 (corresponding to P=0.05 Bonferroni-corrected for 500,000 comparisons), variation coefficient of RAS-derived allelic frequencies=0.2.

Example 2

Whole-genome Scan in the United States Sample

Both the KIBRA rs17070145 and the CLSTN2 rs6439886 SNPs were further evaluated in a second, independent population of 256 cognitively normal older participants (54.1±12.0 years of age) from the United States. The KIBRA SNP showed significant association with episodic memory with the same direction of effect: T allele carriers had significantly better memory scores than non-carriers in the Rey Auditory Verbal Learning Test (AVLT) (12) and Buschke's Selective Reminding Test (SRT) (13) (Table 2). This effect was independent of the presence or number of the apolipoprotein E □4 (APOE4) alleles in these older participants (P=0.5, data not shown). Importantly, there were no allele-dependent differences in the outcome of the Wisconsin Card Sorting Test and the Paced Auditory Serial Attention Task, suggesting that rs17070145 did not affect executive functions, attention and working memory also in this population. SNP rs6439886 failed to show significant association with episodic memory in this older population. Besides the possibility of false-positivity in the first sample for this particular SNP, the lack of significance in the second population may also be related to differences in ethnicity and mean age between the populations, and thus should not be completely discounted as relevant to memory performance. Both ethnicity and age may influence genotype-phenotype associations, e.g. as they have shown to influence the association between APOE4 and Alzheimer's disease risk (14, 15). We decided to follow up only on the KIBRA SNP because of its highly significant association with episodic memory in both populations.

Materials and Methods.

Memory testing and genotyping was done in 256 cognitively normal subjects (171 females, 85 males; mean age 54.0±0.7 [standard error] years). Participants were recruited through local newspaper advertisements for a longitudinal study on the impact of genetic factors on cognitive functions. Demographic, family, and medical historical data were obtained on each individual undergoing genotyping. All individuals gave their written, informed consent, approved by the Mayo Clinic and Banner Good Samaritan Medical Center Institutional Review Boards. A complete medical history, the Structured Psychiatric Interview for Diagnostic and Statistical Manual of Mental Disorders-III-R, the Folstein Mini-Mental State Examination, the Hamilton Depression Scale and neurologic examination were performed. The Auditory Verbal Learning Test (AVLT) (12) and the Buschke's Selective Reminding Test (SRT) (13) were used to quantify verbal episodic memory. Executive functions, attention and working memory were quantified by the Wisconsin Card Sorting Test and the Paced Auditory Serial Attention Task (13).

Example 3

Linkage Disequilibrium Around the KIBRA Locus

Fine-mapping the genomic region harboring KIBRA and the flanking genes RARS and ODZ2 with 13 additional common SNPs (FIG. 1) was performed to ensure that the observed association of KIBRA SNP rs17070145 with episodic memory was not due to linkage disequilibrium (LD) with genetic variations in nearby genes. Significant LD levels were detected between rs7727920 and rs2279698 (spanning KIBRA 5'-UTR and the first exon), between rs11738934 and rs3733980 (spanning a haplotype block entirely contained within KIBRA), and between rs244903 and rs10516047 (spanning KIBRA 3'-UTR and RARS). SNP rs17070145 and the corresponding KIBRA haplotype yielded the highest significance levels (P=0.000004 and P=0.000008, respectively, FIG. 1). We conclude that the observed association is unrelated to LD with adjacent genes.

Materials and Methods

Individual Genotyping

Genotyping of SNPs rs17070145 (KIBRA) and rs6439886 (CLSTN2) in the Swiss and US samples was done by Pyrosequencing™ (Uppsala, Sweden) on a PSQ 96 MA machine. Primers for KIBRA rs17070145 SNP were: 5'-ACA CCT CTG TGG CTT TTC TCC-3' (SEQ ID NO: 5) (forward), 5'-ACA AGG CTG TGG AAT CTC TTG A-3' (SEQ ID NO: 6) (reverse, 5' biotinylated), 5'-CCT TGA TCC TGG ACC-3' (SEQ ID NO: 7) (sequencing primer). Primers for rs6439886 were: 5'-GGG GCA GAG ATT GGT ATT GTC-3' (SEQ ID NO: 8) (forward), 5'-CTA CAG CCC ATT ATG CTC ACC A-3' (SEQ ID NO: 9) (reverse, 5' biotinylated), 5'-AGT CAC TCA TCA CAG TAA TC-3' (SEQ ID NO: 10) (sequencing primer). Individual fine-mapping of the KIBRA region in the Swiss population was done by the Amplifluor method (www.kbiosciences.com). Following SNPs were analyzed: rs1363560, rs7727920, rs2279698, rs11738934, rs6862868, rs2241368, rs17551608, rs4976606, rs3822660, rs3822659, rs3733980, rs244903, and rs10516047.

Genotyping of SNP rs1477306 (KIBRA) in the Swiss sample was done by Pyrosequencing™ (Uppsala, Sweden) on a PSQ 96 MA machine. Primers for KIBRA rs1477306 SNP were: 5'-CTG ATT TGT GAG CGG GGT TTG-3' (forward, 5' biotinylated) (SEQ ID NO: 11), 5'-GGT GCC TTT GAG AGG AAT AGA-3' (SEQ ID NO: 12) (reverse), 5'-AAT AGA CAC ATC CAG GAG A-3'(sequencing primer) (SEQ ID NO: 13).

Statistical Analysis

PowerMarker Version 3.22 (www.powermarker.net) was used for the analysis of linkage disequilibrium and for haplotype reconstruction. Multifactorial analyses of covariance were done for the simultaneous assessment of the influence of age, sex, education, and genotype effects on cognitive test performance. All tests were two-tailed.

Example 4

Gene Expression of KIBRA in the Human Brain

Having established a genetic link between KIBRA and human memory performance, expression levels of KIBRA in the human brain and especially in such memory-related regions as the hippocampus, the frontal and parietal lobe were determined. RT-PCR amplicons were designed detecting both KIBRA full-length transcript and its truncated form KIAA0869, which lacks the first 223 amino acids and which is likely formed through an alternate transcriptional start site (16). Expression levels of full-length KIBRA in the human brain were marginal. In contrast, expression levels of truncated KIBRA were high in all brain regions examined, with highest levels in the hippocampus (FIG. 2). Importantly, SNP rs17070145 maps within the truncated form of KIBRA. KIBRA expression patterns in the human brain are consistent with a role in memory performance.

Materials and Methods
Gene Expression Studies

KIBRA qRT-PCR was done on an ABI PRISM 7700 TaqMan® machine (ABI, Foster City, Calif. USA) using SYBR master mix (Stratagene, Gebouw Calif., Amsterdam, The Netherlands) according to manufacturer's instructions. cDNA from human whole brain homogenate, hippocampus, frontal and parietal lobe was purchased from BioCat (BioCat GmbH, Im Neuenheimer Feld, Heidelberg Germany). Primers were designed by PrimerDesign™ (v1.9, ABI) using CCDS 4366.1 and full-length KIBRA sequence NM_015238. A primer pair recognizing a sequence in exon 2 was designed to detect only full-length KIBRA transcripts (forward: 5'-GCT CAC CTT TGC TGA CTG CA-3' (SEQ ID NO: 14), reverse: 5'-TCC AAC CTG TGG GTC ATA TGC-3' (SEQ ID NO: 15)). A primer pair recognizing a sequence in exon 15 was designed to detect full length and truncated KIBRA transcripts containing exon 15 (forward: 5'-GGC CTC TGG ACG CCT CA-3' (SEQ ID NO: 16), reverse: 5'-TGG TGA AGG GCT GGA TAG GA-3' (SEQ ID NO: 17)). An intronic primer pair was designed to detect eventual genomic contamination (forward: 5'-TGG GCT CAA ACA TTC AAC CTG-3' (SEQ ID NO: 18), reverse: 5'-ACG CTG GCT CAT GCC TGT A-3' (SEQ ID NO: 19)).

Example 5

KIBRA Allele-Dependent Differences in Hippocampal Function

The impact of the KIBRA genotype on memory-related brain functions was investigated using functional magnetic resonance imaging (fMRI). fMRI is a technique which has been used to map brain regions associated with different aspects of human memory (17, 18). Thirty subjects from the Swiss population (15 carriers of the rs17070145*T allele versus 15 non-carriers) underwent fMRI. The allelic groups were matched for sex (5 males and 10 females in each group), education (P=0.7), age (P=0.8), the His452Tyr genotype of the 5-HT2a receptor gene (2) (P 0.4), and for 5-min delayed recall performance (P=1.0). The reason for matching genotype groups for memory performance was to study allele-dependent differences in memory-related brain activity independently of differential performance. Because KIBRA was associated with human episodic memory which depends on the function of the hippocampus (11, 19, 20) and because KIBRA expression was highest in the hippocampus, the hypothesis that KIBRA genotypes might affect episodic memory-related information processing in the human hippocampus was tested. As neuroimaging studies have found that the hippocampus is especially activated by associative episodic memory tasks (18, 21), the impact of the KIBRA genotype on hippocampal activations in a face-profession associative task was tested (21). As expected based on the matching, there were no allele-dependent differences in fMRI retrieval performance (P=0.5). During memory retrieval, non-carriers of the T allele showed significantly increased brain activations compared to T allele carriers in the medial temporal lobe (local maximum in the right hippocampus at coordinate position [26, −12, −14], P<0.001, FIG. 3). Non-carriers of the T allele also showed increased activations in the frontal cortex (local maxima in the right medial frontal gyrus (Brodmann area 8/9) at coordinate position [30, 42, 42], P<0.001, and in the left medial frontal gyrus (Brodmann area 6) at [−24, 10, 56], P<0.001), and in the parietal cortex (local maximum in the right inferior parietal lobulus (Brodmann area 40) at coordinate position [50, −24, 30], P<0.001). In addition to the hippocampus, also these neocortical regions belong to a network important for episodic memory retrieval (17). The present findings therefore suggest that non-carriers of the T allele need more activation in these memory retrieval-related brain regions to reach the same level of retrieval performance as T allele carriers. During memory encoding, no allele-dependent differences in brain activations were found, suggesting that the genotype did not affect episodic memory at this early stage of memory formation. In an additional working memory task, no allele-dependent differences in brain activation in these regions were seen, indicating that the above reported activations in non-carriers were specific to episodic memory retrieval. Automated voxel-based algorithms (SPM2) (22) and manual volume measurements failed to reveal significant allele-dependent differences in the hippocampus or the parahippocampus (P=0.1), suggesting that imaging results were not biased by morphological differences.

Materials and Methods
Subjects 10 males, 20 females; mean age 22.1±0.4 (s.e.) years.

Episodic Memory Task

There were three fMRI time-series (one per learning run) for the intentional learning of face-profession pairs. Each time-series consisted of the face-profession associative learning condition and a visual baseline condition. Sixteen face-profession pairs for associative learning and 24 head contours without physiognomy in the baseline condition were studied. The instruction for associative learning of the face-profession pairs was to imagine the presented person acting in a scene of the written profession. Subjects answered by button press whether they found it easy or hard to imagine a scene. Importantly, subjects were requested to imagine the same scene for a given face-profession pair during runs 2 and 3 as during run 1. The baseline task was to decide whether the area of the left or right ear was larger. Each learning condition consisted of four blocks. A block contained 4 trials of 6 s each. The baseline condition consisted also of 4 blocks. Here, a block contained six trials of 4 s each. Consequently, each task block took 24 s. An instruction slide announced each task block. For retrieval of the previously learned face-profession associations and faces, a single fMRI time-series was applied. This time-series included the associative retrieval condition and the same visual baseline condition that was used for the encoding time-series. For the retrieval of the associations, the previously presented faces were shown again (without the professions) as retrieval cues with the instruction to recall each person's occupation and to indicate the superordinate professional category by button press: academic or workman. The retrieval condition consisted of four blocks, each block including four trials of 6 s each. All task blocks took 24 s and were announced by an instruction slide.

Working Memory

The experiment included one fMRI time-series with a 2-back task for the assessment of working memory and a baseline task ('x-target') for the assessment of concentration. The 2-back task required subjects to respond to a letter repeat with one intervening letter (e.g. S-f-s-g). The 'x-target' task required subjects to respond to the occurrence of the letter 'x'.

Each task was given in five blocks of 26 s each. Blocks were announced by an instruction slide. Stimuli were 50 upper- or lowercase letters typed in black on a white background. Thirteen upper- or lowercase letters were presented per block for the duration of 2 s each.

Data Acquisition

MR measurements were performed on a 3T Philips Intera whole body MR scanner equipped with an eight-channel Philips SENSE head coil. Functional data were obtained from 32 transverse slices parallel to the AC-PC plane covering the whole brain with a measured spatial resolution of 2.8×2.8×4 mm$^3$ (acquisition matrix 80×80) and a reconstructed resolution of 1.7×1.7×4 mm$^3$. Data were acquired using a SENSE-sshEPI (31) sequence with an acceleration factor of R=2.0. Other scan parameters were TE=35 ms, TR=3000 ms. θ=82°. A standard 3D T1-weighted scan was obtained for anatomical reference with a measured spatial resolution of 1×1×1.5 mm$^3$ (acquisition matrix 224×224) and a reconstructed resolution of 0.9×0.9×0.8 mm$^3$, TE=2.3 ms. TR=20 ms, θ=20°. A 2D T1-weighted inversion-recovery anatomical scan, oriented perpendicularly to the long axis of the hippocampus, was obtained for hippocampal and parahippocampal volumetry over 33-39 slices with a measured spatial resolution of 0.5× 0.6×1.5 mm$^3$ (acquisition matrix 400×320) and a reconstructed spatial resolution of 0.4×0.4×1.5 mm$^3$, TE=15 ms, TR=4200 ms, θ=20°, IR delay 400 ms, no interslice gaps.

Analysis of fMRI Data

Image pre- and post-processing and the statistical analyses were performed with SPM2 (www.fil.ion.ucl.ac.uk/spm). Standard preprocessing procedures were applied, i.e., realignment, normalization and spatial smoothing (8 mm) (32). On the single subject level, data were analyzed according to the fixed effects model (SPM2). The six head movement parameters were included in the model as confounding factors. Data were high-pass filtered with a specific filter-value for each fMRI time series. This value was determined according to '2*SOA*TR'. OD the second level, within-subject contrasts were entered into random effects analyses (ANOVAs, T-tests, SPM2) which account for variance between subjects (33). We also computed correlations between the within-subject encoding contrasts (learning run1-run3) and behavioral measures (simple regression, SPM2). Thresholds were set at a p<0.001 level, uncorrected for multiple comparisons.

Analysis of Anatomical MRI Data

Based on the 3D-T1-weighted structural MRI images which covered the whole brain, volumes of the total grey and white matter were computed with SPM2. Images were first normalized into the NM1 T1 template using a standard bounding box and then segmented into grey matter, white matter and cerebrospinal fluid. Standardized grey and white matter volumes were then multiplied by the determinant of the linear transformation matrix to obtain grey and white matter volumes in cm.sup.3. Based on the 2D-T1-weighted high resolution structural MRI images, two independent raters manually delineated the hippocampal formation (18) (CA regions, dentate gyrus and subiculum, excluding the fimbria) and the parahippocampal gyrus using the software Pmod (www.pmod.com.). Cerebrospinal fluid was carefully excluded which resulted in conservative volume estimates. Inter-rater reliabilities ranged between r=0.8 and 0.98. ANOVAs with APOE genotype and sex as independent variables were computed to determine group differences in brain volumes. Thresholds were set at p<0.05 level, uncorrected for multiple comparisons.

We claim:

1. A method for identifying the presence of a genetic predisposition to decreased memory performance related to SNP rs17070145 in a human subject, said method comprising:
   a. detecting in said subject the presence of a C allele at SNP rs17070145 in both copies of the KIBRA gene; and
   b. correlating the presence of a C allele at SNP rs17070145 in both copies of the KIBRA gene with the presence of a genetic predisposition to decreased memory performance related to SNP rs17070145 in said subject.

2. The method of claim 1 wherein the nucleotide content present in a combination of two or more SNPs is detected.

3. The method of claim 1, further comprising detecting in said subject the nucleotide content that is present in at least one KIBRA gene single nucleotide polymorphism selected from the group consisting of SNP rs17551608, rs1477306, rs4976606, rs3822660 and rs3822659.

4. The method of claim 1, further comprising detecting in said subject the nucleotide content that is present in the KIBRA gene single nucleotide polymorphisms rs17551608 and rs1477306.

5. A method for identifying the absence of a genetic predisposition to decreased memory performance related to SNP rs17070145 in a human subject, said method comprising:

a. detecting in said subject the presence of a T allele at SNP rs17070145 in at least one copy of the KIBRA gene; and
b. correlating the presence of a T allele at SNP rs17070145 in at least one copy of the KIBRA gene with the absence of a genetic predisposition to decreased memory performance related to SNP rs17070145 in said subject.

6. The method of claim 5 wherein the nucleotide content present in a combination of two or more SNPs is detected.

7. The method of claim 5, further comprising detecting in said subject the nucleotide content that is present in at least one KIBRA gene single nucleotide polymorphism selected from the group consisting of SNP rs17551608, rs1477306, rs4976606, rs3822660 and rs3822659.

8. The method of claim 5, further comprising detecting in said subject the nucleotide content that is present in the KIBRA gene single nucleotide polymorphisms rs17551608 and rs1477306.

* * * * *

```
                         SEQUENCE LISTING

<160> NUMBER OF SEQ ID NOS: 19

<210> SEQ ID NO 1
<211> LENGTH: 3342
<212> TYPE: DNA
<213> ORGANISM: Homo sapiens

<400> SEQUENCE: 1
atgccccggc cggagctgcc cctgccggag ggctgggagg aggcgcgcga cttcgacggc      60
aaggtctact acatagacca cacgaaccgc accaccagct ggatcgaccc gcgggacagg     120
tacaccaaac cgctcacctt tgctgactgc attagtgatg agttgccgct aggatgggaa     180
gaggcatatg acccacaggt tggagattac ttcatagacc acaacaccaa aaccactcag     240
attgaggatc ctcgagtaca atggcggcgg gagcaggaac atatgctgaa ggattacctg     300
gtggtggccc aggaggctct gagtgcacaa aaggagatct accaggtgaa gcagcagcgc     360
ctggagcttg cacagcagga gtaccagcaa ctgcatgccg tctgggagca taagctgggc     420
tcccaggtca gcttggtctc tggttcatca tccagctcca agtatgaccc tgagatcctg     480
aaagctgaaa ttgccactgc aaaatcccgg gtcaacaagc tgaagagaga gatggttcac     540
ctccagcacg agctgcagtt caaagagcgt ggctttcaga ccctgaagaa aatcgataag     600
aaaatgtctg atgctcaggg cagctacaaa ctggatgaag ctcaggctgt cttgagagaa     660
acaaaagcca tcaaaaaggc tattacctgt ggggaaaagg aaaagcaaga tctcattaag     720
agccttgcca tgttgaagga cggcttccgc actgacaggg ggtctcactc agacctgtgg     780
```

```
tccagcagca gctctctgga gagttcgagt ttcccgctac cgaaacagta cctggatgtg    840
agctcccaga cagacatctc gggaagcttc ggcatcaaca gcaacaatca gttggcagag    900
aaggtcagat tgcgccttcg atatgaagag gctaagagaa ggatcgccaa cctgaagatc    960
cagctggcca agcttgacag tgaggcctgg cctggggtgc tggactcaga gagggaccgg   1020
ctgatcctta tcaacgagaa ggaggagctg ctgaaggaga tgcgcttcat cagcccccgc   1080
aagtggaccc aggggaggt ggagcagctg agatggccc ggaagcggct ggaaaaggac   1140
ctgcaggcag cccgggacac ccagagcaag gcgctgacgg agaggttaaa gttaaacagt   1200
aagaggaacc agcttgtgag agaactggag gaagccaccc ggcaggtggc aactctgcac   1260
tcccagctga aaagtctctc aagcagcatg cagtccctgt cctcaggcag cagccccgga   1320
tccctcacgt ccagccgggg ctccctggtt gcatccagcc tggactcctc cacttcagcc   1380
agcttcactg acctctacta tgaccccttt gagcagctgg actcagagct gcagagcaag   1440
gtggagttcc tgctcctgga gggggccacc ggcttccggc cctcaggctg catcaccacc   1500
atccacgagg atgaggtggc caagacccag aaggcagagg gaggtggccg cctgcaggct   1560
ctgcgttccc tgtctggcac cccaaagtcc atgacctccc tatccccacg ttcctctctc   1620
tcctcccct ccccaccctg ttcccctctc atggctgacc cctcctggc tggtgatgcc   1680
ttcctcaact ccttggagtt tgaagacccg gagctgagtg ccactctttg tgaactgagc   1740
cttggtaaca gcgcccagga aagataccgg ctggaggaac caggaacgga gggcaagcag   1800
ctgggccaag ctgtgaatac ggcccagggg tgtggcctga agtggcctg tgtctcagcc   1860
gccgtatcgg acgagtcagt ggctggagac agtggtgtgt acgaggcttc cgtgcagaga   1920
ctgggtgctt cagaagctgc tgcatttgac agtgacgaat cggaagcagt gggtgcgacc   1980
cgaattcaga ttgccctgaa gtatgatgag aagaataagc aatttgcaat attaatcatc   2040
cagctgagta accttttctgc tctgttgcag caacaagacc agaaagtgaa tatccgcgtg   2100
gctgtccttc cttgctctga aagcacaacc tgcctgttcc ggacccggcc tctggacgcc   2160
tcagacactc tagtgttcaa tgaggtgttc tgggtatcca tgtcctatcc agcccttcac   2220
cagaagacct taagagtcga tgtctgtacc accgacagga gccatctgga agagtgcctg   2280
ggaggcgccc agatcagcct ggcggaggtc tgccggtctg gggagaggtc gactcgctgg   2340
tacaaccttc tcagctacaa atacttgaag aaacagagca gggagctcaa gccagtggga   2400
gtcatggccc ctgcctcagg gcctgccagc acggacgctg tgtctgctct gttggaacag   2460
acagcagtgg agctggagaa gaggcaggag gcaggagca gcacacagac actgaagac   2520
agctggaggt atgaggagac cagtgagaat gaggcagtag ccgaggaaga ggaggaggag   2580
gtggaggagg aggagggaga agaggatgtt ttcaccgaga aagcctcacc tgatatggat   2640
gggtacccag cattaaaggt ggacaaagag accaacacgg agaccccggc cccatccccc   2700
acagtggtgc gacctaagga ccggagagtg ggcaccccgt cccagggggcc atttcttcga   2760
gggagcacca tcatccgctc taagaccttc tccccaggac cccagagcca gtacgtgtgc   2820
cggctgaatc ggagtgatag tgacagctcc actctgtcca aaaagccacc tttttgttcga   2880
aactccctgg agcgacgcag cgtccggatg aagcggcctt cctcggtcaa gtcgctgcgc   2940
tccgagcgtc tgatccgtac ctcgctcgac ctggagttag acctgcaggc gacaagaacc   3000
tggcacagcc aattgaccca ggagatctcg gtgctgaagg agctcaagga gcagctggaa   3060
caagccaaga gccacgggga gaaggagctg ccacagtggt tgcgtgagga cgagcgtttc   3120
cgcctgctgc tgaggatgct ggagaagcgg cagatggacc gagcggagca aagggtgag   3180
```

-continued

```
cttcagacag acaagatgat gagggcagct gccaaggatg tgcacaggct ccgaggccag      3240
agctgtaagg aaccccccaga agttcagtct ttcaggggaga agatggcatt tttcacccgg    3300
cctcggatga atatcccagc tctctctgca gatgacgtct aa                        3342
```

<210> SEQ ID NO 2
<211> LENGTH: 2670
<212> TYPE: DNA
<213> ORGANISM: Artificial Sequence
<220> FEATURE:
<223> OTHER INFORMATION: Description of Artificial Sequence: DNA
      encoding truncated Kibra protein

<400> SEQUENCE: 2

```
aaaaaggcta ttacctgtgg ggaaaaggaa aagcaagatc tcattaagag ccttgccatg       60
ttgaaggacg gcttccgcac tgacaggggg tctcactcag acctgtggtc cagcagcagc      120
tctctggaga gttcgagttt cccgctaccg aaacagtacc tggatgtgag ctcccagaca      180
gacatctcgg gaagcttcgg catcaacagc aacaatcagt ggcagagaaa ggtcagattg      240
cgccttcgat atgaagaggc taagagaagg atcgccaacc tgaagatcca gctggccaag      300
cttgacagtg aggcctggcc tggggtgctg gactcagaga gggaccggct gatccttatc      360
aacgagaagg aggagctgct gaaggagatg cgcttcatca gccccccgcaa gtggacccag      420 ggggaggtgg agcagctgga gatggcccgg aagcggctgg aaaaggacct gcaggcagcc      480
cgggacaccc agagcaaggc gctgacggag aggttaaagt taaacagtaa gaggaaccag      540
cttgtgagaa aactggagga agccaccccgg caggtggcaa ctctgcactc ccagctgaaa      600
agtctctcaa gcagcatgca gtccctgtcc tcaggcagca gccccggatc cctcacgtcc      660
agccggggct ccctggttgc atccagcctg gactcctcca cttcagccag cttcactgac      720
ctctactatg accccttttga gcagctggac tcagagctgc agagcaaggt ggagttcctg      780
ctcctggagg gggccaccgg cttccggccc tcaggctgca tcaccaccat ccacgaggat      840
gaggtggcca agaccccagaa ggcagaggga ggtggccgcc tgcaggctct gcgttccctg      900
tctggcaccc caaagtccat gacctcccta tccccacgtt cctctctctc ctccccctcc      960
ccaccctgtt cccctctcat ggctgaccccc ctcctggctg gtgatgcctt cctcaactcc     1020
ttggagtttg aagacccgga gctgagtgcc actctttgtg aactgagcct tggtaacagc     1080
gcccaggaaa gataccggct ggaggaacca ggaacggagg gcaagcagct gggccaagct     1140
gtgaatacgg cccagggggtg tggcctgaaa gtggcctgtg tctcagccgc cgtatcggac     1200
gagtcagtgg ctggagacag tggtgtgtac gaggcttccg tgcagagact gggtgcttca     1260
gaagctgctg catttgacag tgacgaatcg aagcagtgg gtgcgacccg aattcagatt     1320
gccctgaagt atgatgagaa gaataagcaa tttgcaatat taatcatcca gctgagtaac     1380
ctttctgctc tgttgcagca acaagaccag aaagtgaata tccgcgtggc tgtccttcct     1440
tgctctgaaa gcacaaccctg cctgttccgg acccggcctc tggacgcctc agacactcta     1500
gtgttcaatg aggtgttctg ggtatccatg tcctatccag cccttcacca gaagaccttaa   1560 agagtcgatg tctgtaccac cgacaggagc catctgaag agtgcctggg aggcgcccag      1620
atcagcctgg cggaggtctg ccggtctggg gagaggtcga ctcgctggta caaccttctc      1680
agctacaaat acttgaagaa acagagcagg gagctcaagc cagtgggagt catggcccct      1740
gcctcagggc ctgccagcac ggacgctgtg tctgctctgt tggaacagac agcagtggag      1800
ctggagaaga ggcaggaggg caggagcagc acacagacac tggaagacag ctggaggtat     1860
gaggagacca gtgagaatga ggcagtagcc gaggaagagg aggaggaggt ggaggaggag     1920
```

```
gagggagaag aggatgtttt caccgagaaa gcctcacctg atatggatgg gtacccagca    1980
ttaaaggtgg acaaagagac caacacggag accccggccc catcccccac agtggtgcga    2040
cctaaggacc ggagagtggg caccccgtcc caggggccat ttcttcgagg gagcaccatc    2100
atccgctcta agaccttctc cccaggaccc cagagccagt acgtgtgccg gctgaatcgg    2160
agtgatagtg acagctccac tctgtccaaa agccaccttt tgttcgaaa ctccctggag    2220 cgacgcagcg tccggatgaa gcggccttcc tcggtcaagt cgctgcgctc cgagcgtctg    2280
atccgtacct cgctggacct ggagttagac ctgcaggcga caagaacctg cacagccaa    2340 ttgacccagg agatctcggt gctgaaggag ctcaaggagc agctggaaca agccaagagc    2400
cacggggaga aggagctgcc acagtggttg cgtgaggacg agcgtttccg cctgctgctg    2460
aggatgctgg agaagcggca gatggaccga gcggagcaca agggtgagct tcagacagac    2520
aagatgatga gggcagctgc caaggatgtg cacaggctcc gaggccagag ctgtaaggaa    2580
cccccagaag ttcagtcttt cagggagaag atggcatttt tcacccggcc tcggatgaat    2640
atcccagctc tctctgcaga tgacgtctaa                                     2670
```

<210> SEQ ID NO 3
<211> LENGTH: 1113
<212> TYPE: PRT
<213> ORGANISM: Homo sapiens

<400> SEQUENCE: 3

```
Met Pro Arg Pro Glu Leu Pro Leu Pro Glu Gly Trp Glu Glu Ala Arg
1               5                   10                  15

Asp Phe Asp Gly Lys Val Tyr Tyr Ile Asp His Thr Asn Arg Thr Thr
                20                  25                  30

Ser Trp Ile Asp Pro Arg Asp Arg Tyr Thr Lys Pro Leu Thr Phe Ala
            35                  40                  45

Asp Cys Ile Ser Asp Glu Leu Pro Leu Gly Trp Glu Glu Ala Tyr Asp
        50                  55                  60

Pro Gln Val Gly Asp Tyr Phe Ile Asp His Asn Thr Lys Thr Thr Gln
65                  70                  75                  80

Ile Glu Asp Pro Arg Val Gln Trp Arg Glu Gln Glu His Met Leu
                85                  90                  95

Lys Asp Tyr Leu Val Val Ala Gln Glu Ala Leu Ser Ala Gln Lys Glu
                100                 105                 110

Ile Tyr Gln Val Lys Gln Gln Arg Leu Glu Leu Ala Gln Gln Glu Tyr
            115                 120                 125

Gln Gln Leu His Ala Val Trp Glu His Lys Leu Gly Ser Gln Val Ser
        130                 135                 140

Leu Val Ser Gly Ser Ser Ser Ser Lys Tyr Asp Pro Glu Ile Leu
145                 150                 155                 160

Lys Ala Glu Ile Ala Thr Ala Lys Ser Arg Val Asn Lys Leu Lys Arg
                165                 170                 175

Glu Met Val His Leu Gln His Glu Leu Gln Phe Lys Glu Arg Gly Phe
                180                 185                 190

Gln Thr Leu Lys Lys Ile Asp Lys Lys Met Ser Asp Ala Gln Gly Ser
            195                 200                 205

Tyr Lys Leu Asp Glu Ala Gln Ala Val Leu Arg Glu Thr Lys Ala Ile
        210                 215                 220

Lys Lys Ala Ile Thr Cys Gly Glu Lys Glu Lys Gln Asp Leu Ile Lys
225                 230                 235                 240
```

-continued

Ser Leu Ala Met Leu Lys Asp Gly Phe Arg Thr Asp Arg Gly Ser His
                245                 250                 255

Ser Asp Leu Trp Ser Ser Ser Ser Leu Glu Ser Ser Ser Phe Pro
    260                 265                 270

Leu Pro Lys Gln Tyr Leu Asp Val Ser Gln Thr Asp Ile Ser Gly
        275                 280                 285

Ser Phe Gly Ile Asn Ser Asn Asn Gln Leu Ala Glu Lys Val Arg Leu
    290                 295                 300

Arg Leu Arg Tyr Glu Glu Ala Lys Arg Arg Ile Ala Asn Leu Lys Ile
305                 310                 315                 320

Gln Leu Ala Lys Leu Asp Ser Glu Ala Trp Pro Gly Val Leu Asp Ser
                325                 330                 335

Glu Arg Asp Arg Leu Ile Leu Ile Asn Glu Lys Glu Leu Leu Lys
            340                 345                 350

Glu Met Arg Phe Ile Ser Pro Arg Lys Trp Thr Gln Gly Glu Val Glu
                355                 360                 365

Gln Leu Glu Met Ala Arg Lys Arg Leu Glu Lys Asp Leu Gln Ala Ala
    370                 375                 380

Arg Asp Thr Gln Ser Lys Ala Leu Thr Glu Arg Leu Lys Leu Asn Ser
385                 390                 395                 400

Lys Arg Asn Gln Leu Val Arg Glu Leu Glu Glu Ala Thr Arg Gln Val
                405                 410                 415

Ala Thr Leu His Ser Gln Leu Lys Ser Leu Ser Ser Met Gln Ser
            420                 425                 430

Leu Ser Ser Gly Ser Ser Pro Gly Ser Leu Thr Ser Ser Arg Gly Ser
    435                 440                 445

Leu Val Ala Ser Ser Leu Asp Ser Ser Thr Ser Ala Ser Phe Thr Asp
450                 455                 460

Leu Tyr Tyr Asp Pro Phe Glu Gln Leu Asp Ser Glu Leu Gln Ser Lys
465                 470                 475                 480

Val Glu Phe Leu Leu Leu Glu Gly Ala Thr Gly Phe Arg Pro Ser Gly
                485                 490                 495

Cys Ile Thr Thr Ile His Glu Asp Glu Val Ala Lys Thr Gln Lys Ala
            500                 505                 510

Glu Gly Gly Gly Arg Leu Gln Ala Leu Arg Ser Leu Ser Gly Thr Pro
    515                 520                 525

Lys Ser Met Thr Ser Leu Ser Pro Arg Ser Ser Leu Ser Ser Pro Ser
530                 535                 540

Pro Pro Cys Ser Pro Leu Met Ala Asp Pro Leu Leu Ala Gly Asp Ala
545                 550                 555                 560

Phe Leu Asn Ser Leu Glu Phe Glu Asp Pro Glu Leu Ser Ala Thr Leu
                565                 570                 575

Cys Glu Leu Ser Leu Gly Asn Ser Ala Gln Glu Arg Tyr Arg Leu Glu
            580                 585                 590

Glu Pro Gly Thr Glu Gly Lys Gln Leu Gly Gln Ala Val Asn Thr Ala
    595                 600                 605

Gln Gly Cys Gly Leu Lys Val Ala Cys Val Ser Ala Ala Val Ser Asp
610                 615                 620

Glu Ser Val Ala Gly Asp Ser Gly Val Tyr Glu Ala Ser Val Gln Arg
625                 630                 635                 640

Leu Gly Ala Ser Glu Ala Ala Ala Phe Asp Ser Asp Glu Ser Glu Ala
                645                 650                 655

Val Gly Ala Thr Arg Ile Gln Ile Ala Leu Lys Tyr Asp Glu Lys Asn
            660                 665                 670

-continued

```
Lys Gln Phe Ala Ile Leu Ile Ile Gln Leu Ser Asn Leu Ser Ala Leu
            675                 680                 685
Leu Gln Gln Gln Asp Gln Lys Val Asn Ile Arg Val Ala Val Leu Pro
            690                 695                 700
Cys Ser Glu Ser Thr Thr Cys Leu Phe Arg Thr Arg Pro Leu Asp Ala
705                 710                 715                 720
Ser Asp Thr Leu Val Phe Asn Glu Val Phe Trp Val Ser Met Ser Tyr
                725                 730                 735
Pro Ala Leu His Gln Lys Thr Leu Arg Val Asp Val Cys Thr Thr Asp
            740                 745                 750
Arg Ser His Leu Glu Glu Cys Leu Gly Gly Ala Gln Ile Ser Leu Ala
            755                 760                 765
Glu Val Cys Arg Ser Gly Glu Arg Ser Thr Arg Trp Tyr Asn Leu Leu
            770                 775                 780
Ser Tyr Lys Tyr Leu Lys Lys Gln Ser Arg Glu Leu Lys Pro Val Gly
785                 790                 795                 800
Val Met Ala Pro Ala Ser Gly Pro Ala Ser Thr Asp Ala Val Ser Ala
                805                 810                 815
Leu Leu Glu Gln Thr Ala Val Glu Leu Glu Lys Arg Gln Glu Gly Arg
            820                 825                 830
Ser Ser Thr Gln Thr Leu Glu Asp Ser Trp Arg Tyr Glu Glu Thr Ser
            835                 840                 845
Glu Asn Glu Ala Val Ala Glu Glu Glu Glu Val Glu Glu Glu
            850                 855                 860
Glu Gly Glu Glu Asp Val Phe Thr Glu Lys Ala Ser Pro Asp Met Asp
865                 870                 875                 880
Gly Tyr Pro Ala Leu Lys Val Asp Lys Glu Thr Asn Thr Glu Thr Pro
                885                 890                 895
Ala Pro Ser Pro Thr Val Val Arg Pro Lys Asp Arg Val Gly Thr
            900                 905                 910
Pro Ser Gln Gly Pro Phe Leu Arg Gly Ser Thr Ile Ile Arg Ser Lys
            915                 920                 925
Thr Phe Ser Pro Gly Pro Gln Ser Gln Tyr Val Cys Arg Leu Asn Arg
            930                 935                 940
Ser Asp Ser Asp Ser Ser Thr Leu Ser Lys Lys Pro Pro Phe Val Arg
945                 950                 955                 960
Asn Ser Leu Glu Arg Arg Ser Val Arg Met Lys Arg Pro Ser Ser Val
                965                 970                 975
Lys Ser Leu Arg Ser Glu Arg Leu Ile Arg Thr Ser Leu Asp Leu Glu
            980                 985                 990
Leu Asp Leu Gln Ala Thr Arg Thr Trp His Ser Gln Leu Thr Gln Glu
            995                 1000                1005
Ile Ser Val Leu Lys Glu Leu Lys Glu Gln Leu Glu Gln Ala Lys
            1010                1015                1020
Ser His Gly Glu Lys Glu Leu Pro Gln Trp Leu Arg Glu Asp Glu
            1025                1030                1035
Arg Phe Arg Leu Leu Leu Arg Met Leu Glu Lys Arg Gln Met Asp
            1040                1045                1050
Arg Ala Glu His Lys Gly Glu Leu Gln Thr Asp Lys Met Met Arg
            1055                1060                1065
Ala Ala Ala Lys Asp Val His Arg Leu Arg Gly Gln Ser Cys Lys
            1070                1075                1080
Glu Pro Pro Glu Val Gln Ser Phe Arg Glu Lys Met Ala Phe Phe
```

```
                    1085                1090                1095

Thr Arg  Pro Arg Met Asn Ile  Pro Ala Leu Ser Ala  Asp Asp Val
         1100                1105                1110

<210> SEQ ID NO 4
<211> LENGTH: 888
<212> TYPE: PRT
<213> ORGANISM: Artificial Sequence
<220> FEATURE:
<223> OTHER INFORMATION: Description of Artificial Sequence: Truncated
      KIBRA protein

<400> SEQUENCE: 4

Lys Lys Ala Ile Thr Cys Gly Glu Lys Glu Lys Gln Asp Leu Ile Lys
1               5                   10                  15

Ser Leu Ala Met Leu Lys Asp Gly Phe Arg Thr Asp Arg Gly Ser His
            20                  25                  30

Ser Asp Leu Trp Ser Ser Ser Ser Leu Glu Ser Ser Ser Phe Pro
            35                  40                  45

Leu Pro Lys Gln Tyr Leu Asp Val Ser Ser Gln Thr Asp Ile Ser Gly
    50                  55                  60

Ser Phe Gly Ile Asn Ser Asn Asn Gln Leu Ala Glu Lys Val Arg Leu
65                  70                  75                  80

Arg Leu Arg Tyr Glu Glu Ala Lys Arg Arg Ile Ala Asn Leu Lys Ile
                85                  90                  95

Gln Leu Ala Lys Leu Asp Ser Glu Ala Trp Pro Gly Val Leu Asp Ser
            100                 105                 110

Glu Arg Asp Arg Leu Ile Leu Ile Asn Glu Lys Glu Glu Leu Leu Lys
        115                 120                 125

Glu Met Arg Phe Ile Ser Pro Arg Lys Trp Thr Gln Gly Glu Val Glu
    130                 135                 140

Gln Leu Glu Met Ala Arg Lys Arg Leu Glu Lys Asp Leu Gln Ala Ala
145                 150                 155                 160

Arg Asp Thr Gln Ser Lys Ala Leu Thr Glu Arg Leu Lys Leu Asn Ser
                165                 170                 175

Lys Arg Asn Gln Leu Val Arg Glu Leu Glu Glu Ala Thr Arg Gln Val
            180                 185                 190

Ala Thr Leu His Ser Gln Leu Lys Ser Leu Ser Ser Ser Met Gln Ser
        195                 200                 205

Leu Ser Ser Gly Ser Ser Pro Gly Ser Leu Thr Ser Ser Arg Gly Ser
    210                 215                 220

Leu Val Ala Ser Ser Leu Asp Ser Ser Thr Ser Ala Ser Phe Thr Asp
225                 230                 235                 240

Leu Tyr Tyr Asp Pro Phe Glu Gln Leu Asp Ser Glu Leu Gln Ser Lys
                245                 250                 255

Val Glu Phe Leu Leu Leu Glu Gly Ala Thr Gly Phe Arg Pro Ser Gly
            260                 265                 270

Cys Ile Thr Thr Ile His Glu Asp Glu Val Ala Lys Thr Gln Lys Ala
        275                 280                 285

Glu Gly Gly Gly Arg Leu Gln Ala Leu Arg Ser Leu Ser Gly Thr Pro
    290                 295                 300

Lys Ser Met Thr Ser Leu Ser Pro Arg Ser Ser Leu Ser Ser Pro Ser
305                 310                 315                 320

Pro Pro Cys Ser Pro Leu Met Ala Asp Pro Leu Leu Ala Gly Asp Ala
                325                 330                 335

Phe Leu Asn Ser Leu Glu Phe Glu Asp Pro Glu Leu Ser Ala Thr Leu
```

340                 345                 350
Cys Glu Leu Ser Leu Gly Asn Ser Ala Gln Glu Arg Tyr Arg Leu Glu
            355                 360                 365

Glu Pro Gly Thr Glu Gly Lys Gln Leu Gly Gln Ala Val Asn Thr Ala
370                 375                 380

Gln Gly Cys Gly Leu Lys Val Ala Cys Val Ser Ala Ala Val Ser Asp
385                 390                 395                 400

Glu Ser Val Ala Gly Asp Ser Gly Val Tyr Glu Ala Ser Val Gln Arg
                405                 410                 415

Leu Gly Ala Ser Glu Ala Ala Ala Phe Asp Ser Asp Glu Ser Glu Ala
            420                 425                 430

Val Gly Ala Thr Arg Ile Gln Ile Ala Leu Lys Tyr Asp Glu Lys Asn
            435                 440                 445

Lys Gln Phe Ala Ile Leu Ile Ile Gln Leu Ser Asn Leu Ser Ala Leu
        450                 455                 460

Leu Gln Gln Gln Asp Gln Lys Val Asn Ile Arg Val Ala Val Leu Pro
465                 470                 475                 480

Cys Ser Glu Ser Thr Thr Cys Leu Phe Arg Thr Arg Pro Leu Asp Ala
                485                 490                 495

Ser Asp Thr Leu Val Phe Asn Glu Val Phe Trp Val Ser Met Ser Tyr
            500                 505                 510

Pro Ala Leu His Gln Lys Thr Leu Arg Val Asp Val Cys Thr Thr Asp
            515                 520                 525

Arg Ser His Leu Glu Glu Cys Leu Gly Gly Ala Gln Ile Ser Leu Ala
        530                 535                 540

Glu Val Cys Arg Ser Gly Glu Arg Ser Thr Arg Trp Tyr Asn Leu Leu
545                 550                 555                 560

Ser Tyr Lys Tyr Leu Lys Lys Gln Ser Arg Glu Leu Lys Pro Val Gly
                565                 570                 575

Val Met Ala Pro Ala Ser Gly Pro Ala Ser Thr Asp Ala Val Ser Ala
            580                 585                 590

Leu Leu Glu Gln Thr Ala Val Glu Leu Glu Lys Arg Gln Glu Gly Arg
        595                 600                 605

Ser Ser Thr Gln Thr Leu Glu Asp Ser Trp Arg Tyr Glu Glu Thr Ser
    610                 615                 620

Glu Asn Glu Ala Val Ala Glu Glu Glu Glu Glu Val Glu Glu Glu
625                 630                 635                 640

Glu Gly Glu Glu Asp Val Phe Thr Glu Lys Ala Ser Pro Asp Met Asp
                645                 650                 655

Gly Tyr Pro Ala Leu Lys Val Asp Lys Glu Thr Asn Thr Glu Thr Pro
            660                 665                 670

Ala Pro Ser Pro Thr Val Val Arg Pro Lys Asp Arg Val Gly Thr
        675                 680                 685

Pro Ser Gln Gly Pro Phe Leu Arg Gly Ser Thr Ile Ile Arg Ser Lys
    690                 695                 700

Thr Phe Ser Pro Gly Pro Gln Ser Gln Tyr Val Cys Arg Leu Asn Arg
705                 710                 715                 720

Ser Asp Ser Asp Ser Ser Thr Leu Ser Lys Lys Pro Pro Phe Val Arg
                725                 730                 735

Asn Ser Leu Glu Arg Arg Ser Val Arg Met Lys Arg Pro Ser Ser Val
            740                 745                 750

Lys Ser Leu Arg Ser Glu Arg Leu Ile Arg Thr Ser Leu Asp Leu Glu
        755                 760                 765

-continued

```
Leu Asp Leu Gln Ala Thr Arg Thr Trp His Ser Gln Leu Thr Gln Glu
        770                 775                 780

Ile Ser Val Leu Lys Glu Leu Lys Glu Gln Leu Glu Gln Ala Lys Ser
785                 790                 795                 800

His Gly Glu Lys Glu Leu Pro Gln Trp Leu Arg Glu Asp Glu Arg Phe
                805                 810                 815

Arg Leu Leu Leu Arg Met Leu Glu Lys Arg Met Asp Arg Ala Glu His
            820                 825                 830

Lys Gly Glu Leu Gln Thr Asp Lys Met Met Arg Ala Ala Ala Lys Asp
        835                 840                 845

Val His Arg Leu Arg Gly Gln Ser Cys Lys Glu Pro Pro Glu Val Gln
    850                 855                 860

Ser Phe Arg Glu Lys Met Ala Phe Phe Thr Arg Pro Arg Met Asn Ile
865                 870                 875                 880

Pro Ala Leu Ser Ala Asp Asp Val
                885

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: KIBRA rs
      17070145 SNP forward primer

<400> SEQUENCE: 5
acacctctgt ggcttttctc c                                               21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: KIBRA rs
      17070145 SNP reverse primer

<400> SEQUENCE: 6
acaaggctgt ggaatctctt ga                                              22

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: KIBRA rs
      17070145 SNP sequencing primer

<400> SEQUENCE: 7
ccttgatcct ggacc                                                      15

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: KIBRA rs
      6439886 SNP forward primer

<400> SEQUENCE: 8
ggggcagaga ttggtattgt c                                               21

<210> SEQ ID NO 9
<211> LENGTH: 22
<212> TYPE: DNA
```

```
<213> ORGANISM: Artificial Sequence
<220> FEATURE:
<223> OTHER INFORMATION: Description of Artificial Sequence: KIBRA rs
      6439886 SNP reverse primer

<400> SEQUENCE: 9
ctacagccca ttatgctcac ca                                                  22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: KIBRA rs
      6439886 SNP sequencing primer

<400> SEQUENCE: 10
agtcactcat cacagtaatc                                                     20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: KIBRA rs
      1477306 SNP forward primer

<400> SEQUENCE: 11
ctgatttgtg agcggggttt g                                                   21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: KIBRA rs
      1477306 SNP reverse primer

<400> SEQUENCE: 12
ggtgcctttg agaggaatag a                                                   21

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: KIBRA rs
      1477306 SNP sequencing primer

<400> SEQUENCE: 13
aatagacaca tccaggaga                                                      19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Kibra
      forward primer

<400> SEQUENCE: 14
gctcaccttt gctgactgca                                                     20

<210> SEQ ID NO 15
<211> LENGTH: 21
<212> TYPE: DNA
<213> ORGANISM: Artificial Sequence
<220> FEATURE:
```

```
<223> OTHER INFORMATION: Description of Artificial Sequence: Kibra
      reverse primer

<400> SEQUENCE: 15
tccaacctgt gggtcatatg c                                              21

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Exon 15
      detection forward primer

<400> SEQUENCE: 16
ggcctctgga cgcctca                                                   17

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Exon 15
      detection reverse primer

<400> SEQUENCE: 17
tggtgaaggg ctggatagga                                                20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Genomic
      contamination detection forward primer

<400> SEQUENCE: 18
tgggctcaaa cattcaacct g                                              21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Genomic
      contamination detection reverse primer

<400> SEQUENCE: 19
acgctggctc atgcctgta                                                 19
```